United States Patent
Tachizaki

(10) Patent No.: US 9,579,495 B2
(45) Date of Patent: Feb. 28, 2017

(54) COVER FOR MALE MEMBER

(71) Applicant: JMS CO., LTD., Hiroshima-shi, Hiroshima (JP)

(72) Inventor: Hitoshi Tachizaki, Hiroshima (JP)

(73) Assignee: JMS Co., Ltd., Hiroshima (JP)

(*) Notice: Subject to any disclaimer, the term of this patent is extended or adjusted under 35 U.S.C. 154(b) by 304 days.

(21) Appl. No.: 14/377,125

(22) PCT Filed: Feb. 14, 2013

(86) PCT No.: PCT/JP2013/053541
§ 371 (c)(1),
(2) Date: Aug. 6, 2014

(87) PCT Pub. No.: WO2013/122148
PCT Pub. Date: Aug. 22, 2013

(65) Prior Publication Data
US 2015/0008664 A1  Jan. 8, 2015

(30) Foreign Application Priority Data
Feb. 15, 2012 (JP) ................. 2012-030874

(51) Int. Cl.
*F16L 35/00* (2006.01)
*A61M 39/02* (2006.01)
(Continued)

(52) U.S. Cl.
CPC .......... *A61M 39/02* (2013.01); *A61M 39/045* (2013.01); *A61M 39/26* (2013.01); *F16L 37/30* (2013.01);
(Continued)

(58) Field of Classification Search
USPC ........ 285/3, 4, 901; 604/244, 246, 247, 249, 604/256, 257; 251/149.1
See application file for complete search history.

(56) References Cited

U.S. PATENT DOCUMENTS 4,342,337 A * 8/1982 Underwood ........... B65D 59/00
138/109
5,690,612 A   11/1997 Lopez et al.
(Continued)

FOREIGN PATENT DOCUMENTS

| EP | 1 820 532 | 8/2007 |
|----|-----------|--------|
| JP | 3389983   | 1/2003 |

(Continued)

OTHER PUBLICATIONS

Extended European Search Report issued in corresponding European Application No. 13749209.6, Sep. 4, 2015, 7 pages.

*Primary Examiner* — Aaron Dunwoody
(74) *Attorney, Agent, or Firm* — Hamre, Schumann, Mueller & Larson, P.C.

(57) ABSTRACT

A head portion (150) is provided at one end of an outer circumferential wall (101) capable of elastic compression deformation. The outer circumferential wall includes multiple compression units (110, 120) that undergo deformation due to compression force in a central axis (100a) direction. Letting N be an integer of 2 or more, the compression units each have at least either N thick portions (113) or N thin portions (123) formed at equiangular intervals with respect to the central axis such that the thickness periodically changes in the circumferential direction. The phase with respect to the central axis of the periodic change in thickness is shifted between two compression units that are neighboring in the central axis direction.

15 Claims, 19 Drawing Sheets

(51) Int. Cl.
*F16L 55/10* (2006.01)
*A61M 39/04* (2006.01)
*A61M 39/26* (2006.01)
*F16L 37/30* (2006.01)

(52) U.S. Cl.
CPC ......... *F16L 55/10* (2013.01); *A61M 2039/263* (2013.01); *A61M 2039/267* (2013.01)

(56) References Cited

U.S. PATENT DOCUMENTS

| | | | | |
|---|---|---|---|---|
| 6,003,715 | A * | 12/1999 | Harris | B67B 7/26 137/587 |
| 6,290,206 | B1 | 9/2001 | Doyle | |
| 6,468,251 | B1 | 10/2002 | Yamanaka et al. | |
| 8,277,424 | B2 * | 10/2012 | Pan | A61M 39/26 604/249 |
| 8,603,048 | B2 * | 12/2013 | Carrez | A61M 39/22 604/246 |
| 2002/0193752 | A1 * | 12/2002 | Lynn | A61M 39/02 604/249 |
| 2003/0209681 | A1 | 11/2003 | Leinsing et al. | |
| 2006/0157971 | A1 | 7/2006 | Baldwin et al. | |
| 2007/0001459 | A1 * | 1/2007 | Wells | F16L 55/11 285/390 |
| 2010/0066073 | A1 * | 3/2010 | Jensen | B60T 13/52 285/3 |
| 2011/0175347 | A1 | 7/2011 | Okiyama | |
| 2011/0178493 | A1 | 7/2011 | Okiyama | |
| 2011/0282302 | A1 | 11/2011 | Lopez et al. | |
| 2016/0199635 | A1 * | 7/2016 | Gagliardoni | A61M 39/26 251/149.1 |

FOREIGN PATENT DOCUMENTS

| | | |
|---|---|---|
| JP | 2003-505158 | 2/2003 |
| JP | 2007-500537 | 1/2007 |
| JP | 4163975 | 8/2008 |
| WO | 01/07102 | 2/2001 |
| WO | 2005/011799 | 2/2005 |
| WO | 2008/052140 | 5/2008 |
| WO | 2010/061742 | 6/2010 |
| WO | 2010/061743 | 6/2010 |
| WO | 2010/111546 | 9/2010 |

* cited by examiner

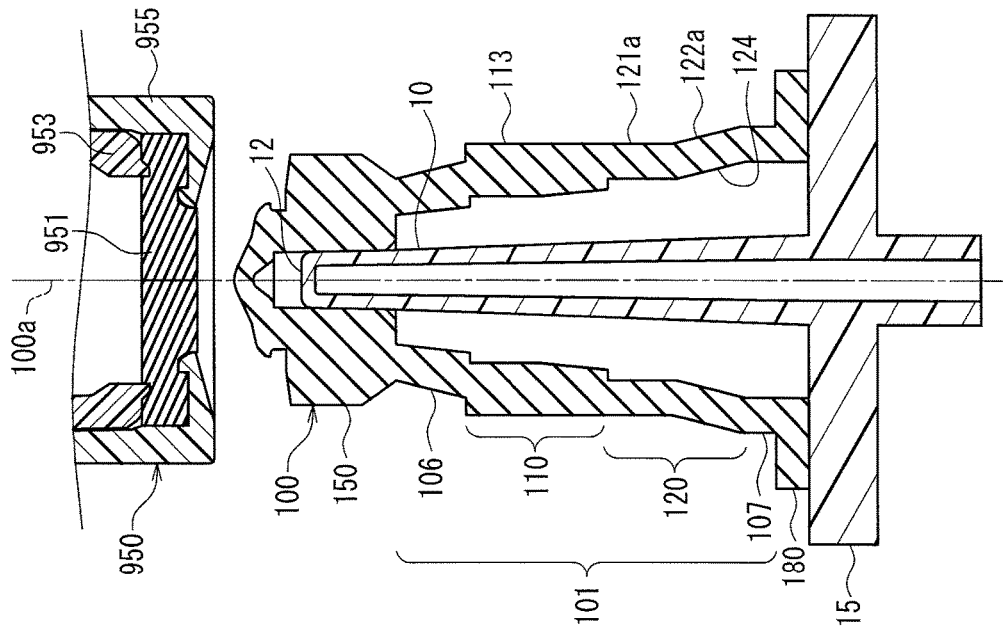
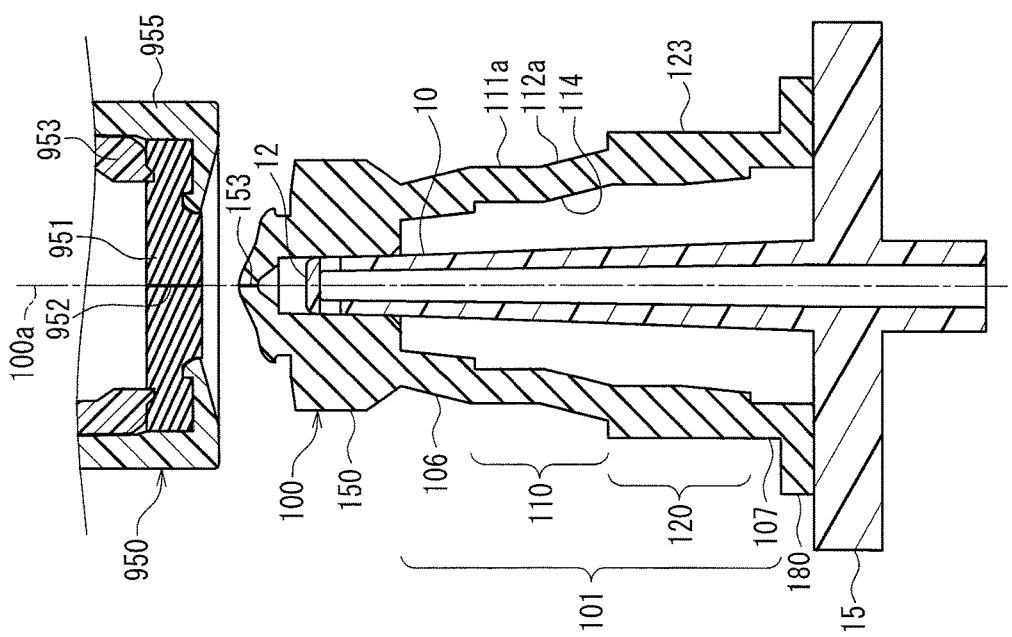
FIG. 8A
FIG. 8B

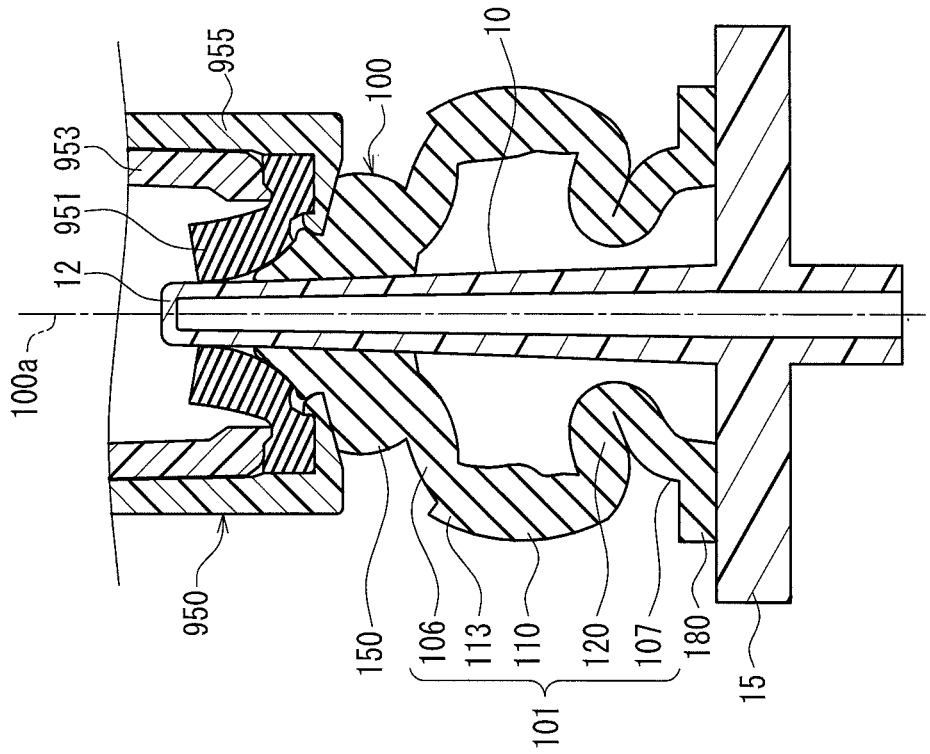
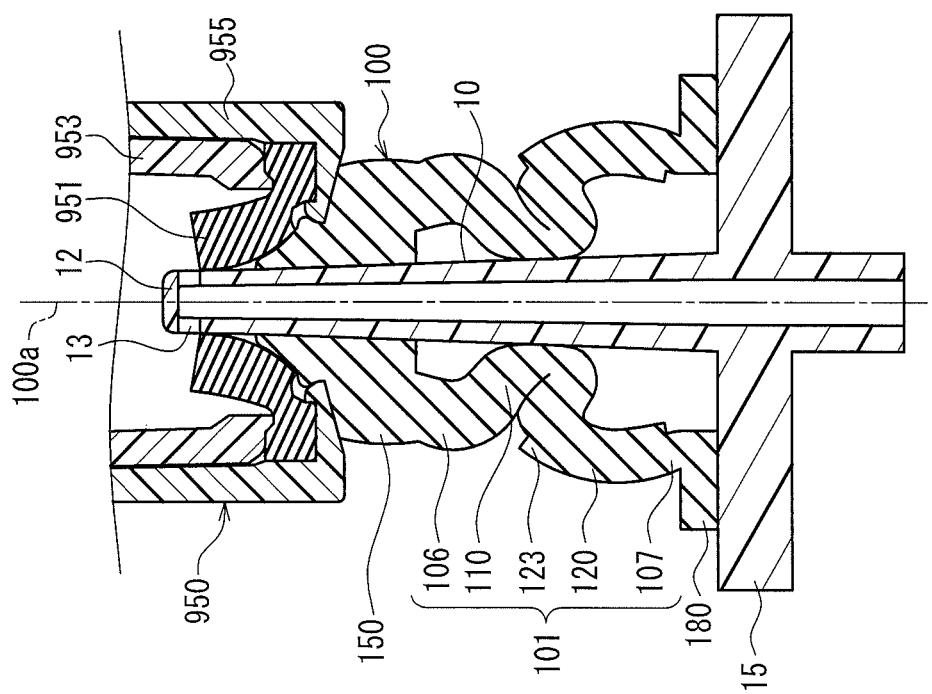
FIG. 9B
FIG. 9A

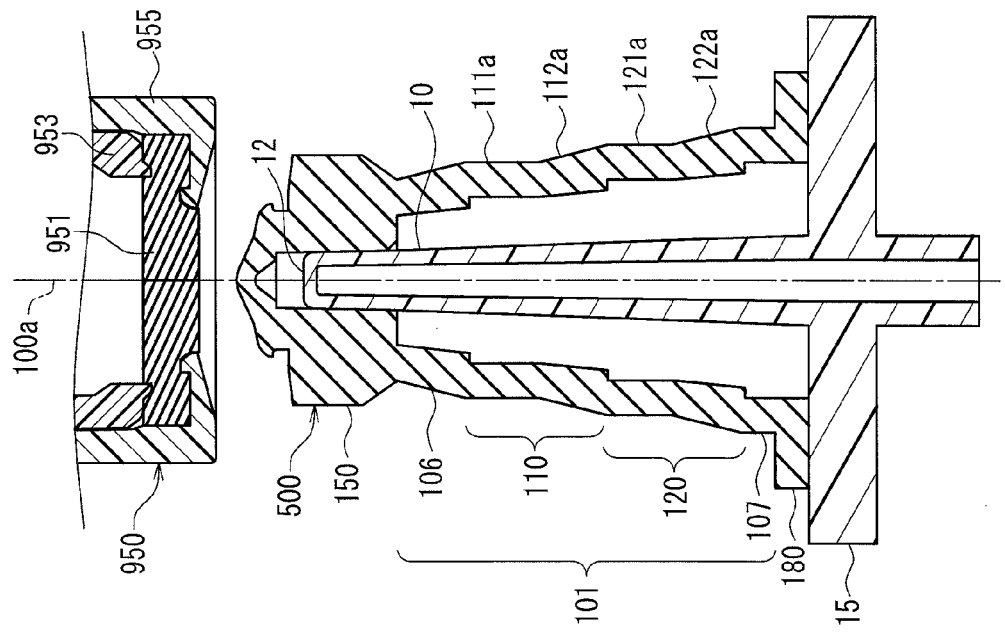
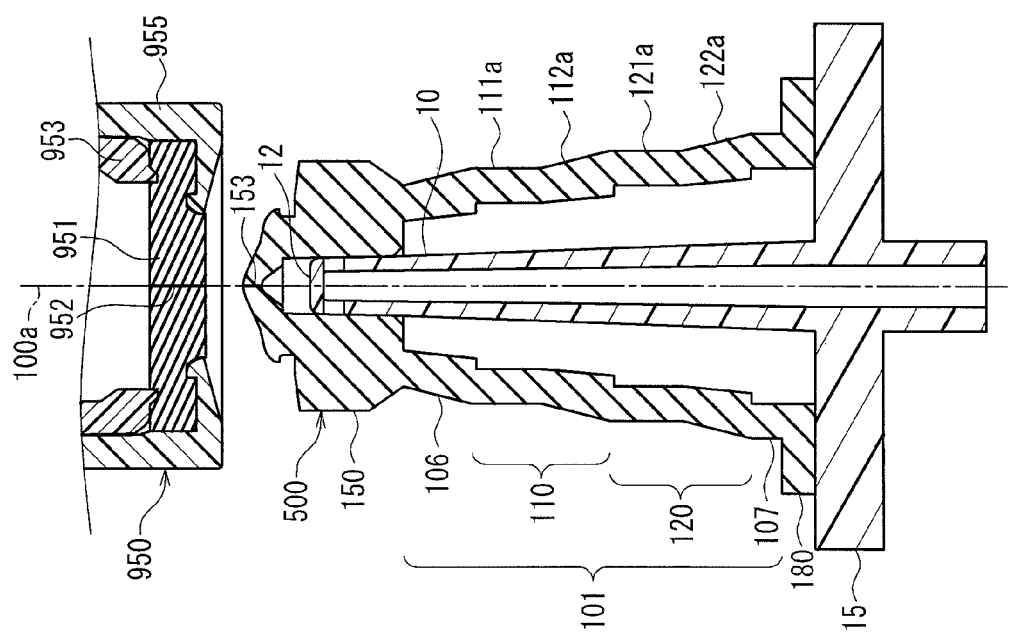
FIG. 10A
FIG. 10B

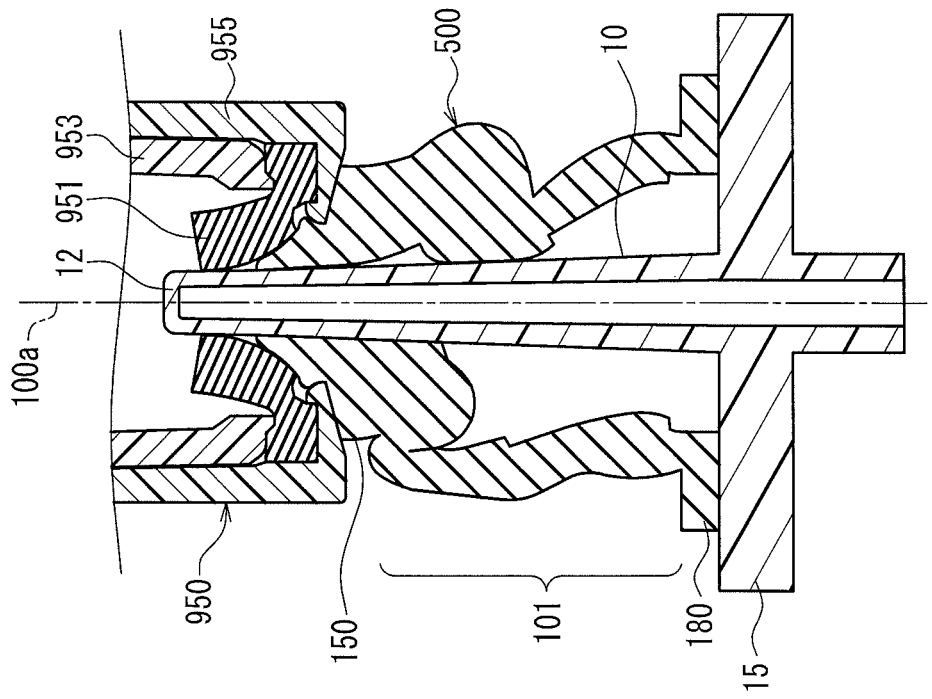
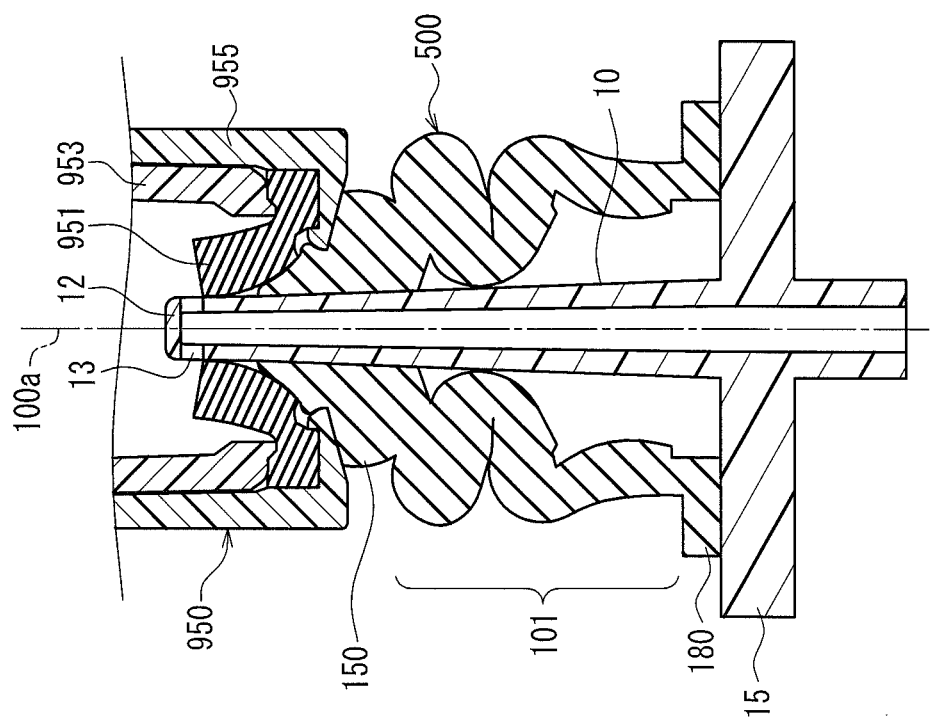

COVER FOR MALE MEMBER

TECHNICAL FIELD

The present invention relates to a cover for a male member that covers at least the tip of a bar-shaped male member in which a flow channel for flow of a liquid is formed.

BACKGROUND ART

When giving a patient an infusion or blood transfusion or performing extracorporeal blood circulation during surgery, it is necessary to form a channel (transport line) for transporting a liquid such as a drug solution or blood. Transport lines are generally formed by connecting containers, various types of instruments, tubes, and the like. One known method for connecting different members is the slip connection of a male luer serving as the male member and a needleless port serving as the female member (e.g., see Patent Documents 1 and 2). The needleless port has a partition wall member (hereinafter referred to as a "septum") that is made of an elastic material such as rubber and has a linear slit (incision) formed in the central portion. The needleless port and the male luer can be put in communication with each other by inserting the male luer (tubular body), which does not have a sharp metal needle such as an injection needle attached thereto, into the slit in the septum. The slit in the septum immediately closes when the male luer is withdrawn from the needleless port. In this way, the septum is resealable, and a male luer repeatedly can be inserted and withdrawn.

There are cases where the drug solution contains a drug designated as a dangerous drug, such as some anticancer drugs. There are also cases where blood contains a pathogen or the like. Accordingly, it is necessary to avoid a situation where a liquid such as a drug solution or blood leaks out and comes into contact with the operator's finger or the like, or the operator inhales vapor from the liquid.

In the above-described slip connection, the slit in the septum immediately closes when the male luer is withdrawn from the needleless port, and therefore there is generally a low possibility of liquid leaking out from the needleless port when the male luer is not connected. However, since the male luer is exposed to the outside before being inserted into the needleless port and after being withdrawn, and there is a possibility of liquid leaking out from the male luer.

In order to reduce the possibility of liquid leaking out from the male luer when it is not connected to the needleless port, there is a known method of covering a male luer 910 with a retractable cover 920 as shown in FIG. 19 (see Patent Documents 3 and 4). The cover 920 includes an outer circumferential wall 921 that has a substantially tubular shape, and one end of the outer circumferential wall 921 is blocked by a top panel 923. The male luer 910 has a tubular shape, and an opening 912 for the inflow and outflow of a liquid is formed in the tip. A linear slit (incision) 925 is formed in the top panel 923 at a position opposing the opening 912 in the male luer 910. A septum 951 of a needleless port 950 is a disc-shaped member made of an elastic material such as rubber, and a linear slit (incision) 952 is formed in the center. The septum 951 is fixed by being sandwiched by a base portion 953 that has a substantially cylindrical shape and a port cap 955.

As shown in FIG. 19, when the male luer 910 is not connected to the needleless port 950, the opening 912 in the male luer 910 is blocked by close contact with the top panel 923 of the cover 920. The slit 925 in the cover 920 is closed. When the male luer 910 is pushed into the needleless port 950 in this state, the male luer 910 passes through the slit 925 in the cover 920 and then passes through the slit 952 in the septum 951, and thus the male luer 910 and the needleless port 950 can be connected. At this time, the outer circumferential wall 921 of the cover 920 undergoes compression deformation due to the compression force applied to the cover 920. Thereafter, when the male luer 910 is withdrawn from the needleless port 950, the outer circumferential wall 921 of the cover 920 extends due to its elastic restoring force and returns to its initial state.

By placing the cover 920 over the male luer 910 as described above, the opening 912 in the male luer 910 can be blocked with the top panel 923 of the cover 920 when the male luer 910 is not connected to the needleless port 950 as shown in FIG. 19. Accordingly, there is a low possibility of liquid leaking out from the male luer 910.

PRIOR ART DOCUMENTS

Patent Document

Patent Document 1: JP 3389983B
Patent Document 2: JP 4163975B
Patent Document 3: WO 2010/061742 (FIG. 7, FIG. 8)
Patent Document 4: WO 2010/061743 (FIG. 10, FIG. 11)

DISCLOSURE OF INVENTION

Problem to be Solved by the Invention

Incidentally, when the male luer 910 provided with the cover 920 is connected to the needleless port 950, there are cases where the outer circumferential wall 921 of the cover 920 does not undergo uniform compression deformation in the lengthwise direction of the male luer 910, but rather undergoes buckling deformation so as to become bent. Since the elastic restoring force generated in the outer circumferential wall 921 that underwent buckling deformation is weak, there is a problem in that even when the male luer 910 is withdrawn from the needleless port 950, the outer circumferential wall 921 of the cover 920 does not completely extend and return to its original state.

An object of the present invention is to resolve the problems with the above-described conventional cover and provide a cover for a male member that does not undergo buckling deformation when subjected to compression force.

Means for Solving Problem

A cover for a male member of the present invention is a cover for a male member that is configured to cover at least a tip of a bar-shaped male member in which a flow channel for flow of a liquid is formed, the cover for a male member including: an outer circumferential wall that has a substantially tubular shape and is capable of elastic compression deformation in a central axis direction of the cover, and a head portion that is provided at one end of the outer circumferential wall and is passed through by the tip of the male member when the outer circumferential wall undergoes compression deformation. The outer circumferential wall includes a plurality of compression units arranged along the central axis direction. The plurality of compression units each undergo deformation due to compression force in the central axis direction. Letting N be an integer of 2 or more, the plurality of compression units each have N thick portions formed at equiangular intervals with respect to the central axis, or have N thin portions formed at equiangular intervals with respect to the central axis, or have both N thick portions and N thin portions formed at equiangular intervals with respect to the central axis. The thickness of each of the plurality of compression units periodically changes in a circumferential direction. A phase with respect to the central axis of the periodic change in thickness is shifted between two compression units that are neighboring in the central axis direction.

Effects of the Invention

According to the present invention, portions that undergo almost no deformation and portions that undergo a large amount of bending deformation when subjected to compression force are formed so as to alternate in the circumferential direction of the compression units. Also, these two different types of portions substantially oppose each other in the central axis direction between adjacent compression units. This makes it possible to provide a cover for a male member that is not likely to undergo buckling deformation.

BRIEF DESCRIPTION OF DRAWINGS

FIGS. 8A and 8B are cross-sectional views showing a state before the male luer having the cover for a male member according to Embodiment 1 of the present invention attached thereto is connected to a needleless port in Experiment 1.

FIGS. 9A and 9B are cross-sectional views showing a state where the male luer having the cover for a male member according to Embodiment 1 of the present invention attached thereto has been connected to the needleless port in Experiment 1.

FIGS. 10A and 10B are cross-sectional views showing a state before a male luer having a cover for a male member according to a comparative example attached thereto is connected to a needleless port in Experiment 1.

FIGS. 11A and 11B are cross-sectional views showing a state where the male luer having the cover for a male member according to the comparative example attached thereto has been connected to the needleless port in Experiment 1.

DESCRIPTION OF THE INVENTION

Figure 1A:
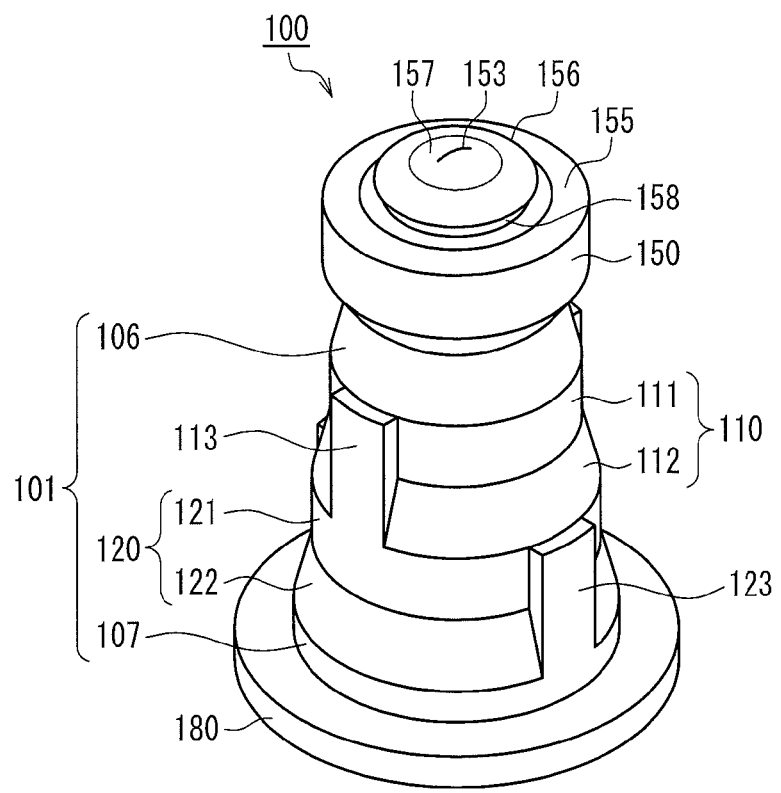
FIG. 1A is a perspective view of a cover for a male member according to Embodiment 1 of the present invention as seen from above.

In the above cover for a male member of the present invention, it is preferable that the N thick portions are each a rib-shaped protruding portion that extends in a direction parallel to the central axis direction. According to this configuration, thick portions having a relatively high mechanical strength can be formed easily with a simple configuration.

Also, it is preferable that the N thin portions are each a groove-shaped receding portion that extends in a direction parallel to the central axis direction. Accordingly, thin portions having a relatively low mechanical strength can be formed easily with a simple configuration.

It is preferable that at least one of the N thick portions and the N thin portions extend over the full length of the compression unit in the central axis direction on which they are formed. According to this configuration, it is possible to make deformation small in portions where deformation is not desired, and make deformation large in portions where deformation is desired. This promotes further preventing the occurrence of buckling deformation while increasing the amount of change in dimension of the cover overall when compression force is applied.

It is preferable that the N thick portions are formed on an outer face of the outer circumferential wall. This helps ensure a large space between the outer circumferential wall and the male member. Accordingly, it is less likely for an impact to occur between the male member and the outer circumferential wall when the outer circumferential wall undergoes compression deformation, and therefore the amount of change in dimension of the cover overall can be increased.

It is preferable that the N thin portions are formed on an inner face of the outer circumferential wall. This helps ensure a large space between the outer circumferential wall and the male member. Accordingly, it is less likely for an impact to occur between the male member and the outer circumferential wall when the outer circumferential wall undergoes compression deformation, and therefore the amount of change in dimension of the cover overall can be increased.

It is preferable that the plurality of compression units each include a forward tapered shape with an outer face and an inner face that are both forward tapered faces such that the diameters increase with increasing distance from the head portion. This enables easily realizing a cover having a substantially forward tapered shape in which the diameter increases with increasing distance from the head portion in a macroscopic view. This enables increasing the amount of change in dimension of the cover overall when compression force is applied. Also, formability is improved since demolding is made easier in the case where the cover is formed using a mold.

In the above configuration, the plurality of compression units each may include a cylindrical shape with an inner face and an outer face that are both cylindrical faces, on the head portion side relative to the forward tapered shape. According to this configuration, formability is improved since demolding is made easier in the case where the cover is formed using a mold.

Alternatively, the plurality of compression units each may include a reverse tapered shape with an inner face and an outer face that are both reverse tapered faces such that the diameters decrease with increasing distance from the head portion, on the head portion side relative to the forward tapered shape. This enables reliably causing portions of the compression units where deformation is desired to undergo deformation when compression force is applied.

It is preferable that the plurality of compression units have substantially similar shapes, and a plurality of compression units having different diameters are arranged such that the diameters of the compression units are higher the farther the compression units are from the head portion. This enables realizing a cover having a substantially forward tapered shape in which the diameter increases with increasing distance from the head portion in a macroscopic view. This enables increasing the amount of change in dimension of the cover overall when compression force is applied. Also, formability is improved since demolding is made easier in the case where the cover is formed using a mold.

It is preferable that a cross-sectional shape of the outer circumferential wall along a plane perpendicular to the central axis at an arbitrary position on the central axis is substantially a circle. This enables further reducing the possibility of buckling deformation of the outer circumferential wall when compression force is applied.

It is preferable that a phase of the periodic change in thickness is shifted by 360/2N degrees with respect to the central axis between two compression units that are neighboring in the central axis direction. According to this configuration, portions that undergo almost no deformation and portions that undergo a large amount of bending deformation when compression force is applied reliably oppose each other in the central axis direction between neighboring compression units. This further promotes preventing the occurrence of buckling deformation while increasing the amount of change in dimension deformation of the cover overall when compression force is applied.

It is preferable that the head portion includes an inner cavity that is configured to receive the tip of the male member. In this case, it is preferable that when the tip of the male member is inserted into the inner cavity, the head portion blocks an opening of the flow channel formed in the male member. This enables further reducing the possibility of leakage of a liquid to the outside.

The male member may be a male luer that includes an outer circumferential face that is a cylindrical face or a tapered face. Alternatively, the male member may be a bottle needle that includes two mutually independent flow channels.

Below, the present invention will be described in detail while disclosing preferred embodiments. However, it goes without saying that the present invention is not limited to the following embodiments. For the sake of convenience in the description, the drawings that are referenced in the following description show simplifications of, among the constituent members of the embodiment of the present invention, only relevant members that are necessary for describing the present invention. The present invention therefore can include arbitrary constituent members that are not shown in the following drawings. Also, regarding the dimensions of the members in the drawings, the dimensions of the actual constituent members, the ratios of the dimensions of the members, and the like are not shown faithfully.

Embodiment 1

Figure 1B:
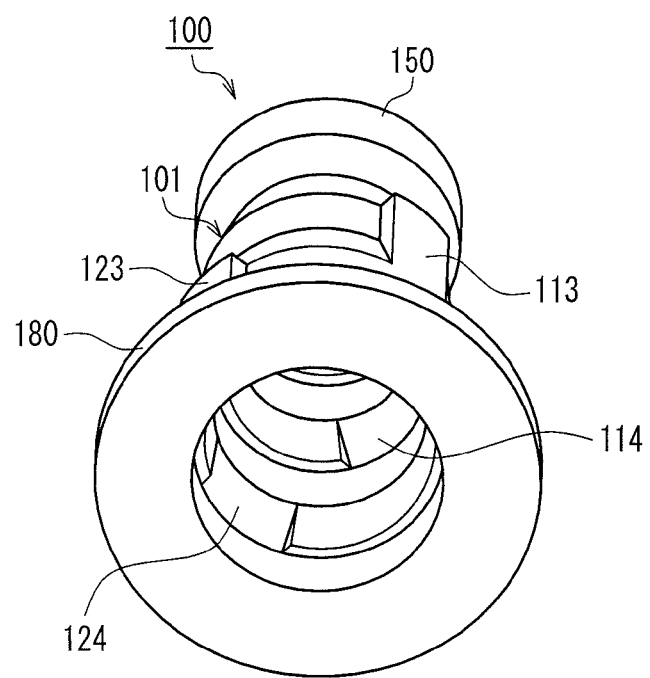
FIG. 1B is a perspective view of the same as seen from below.
Figure 2A:
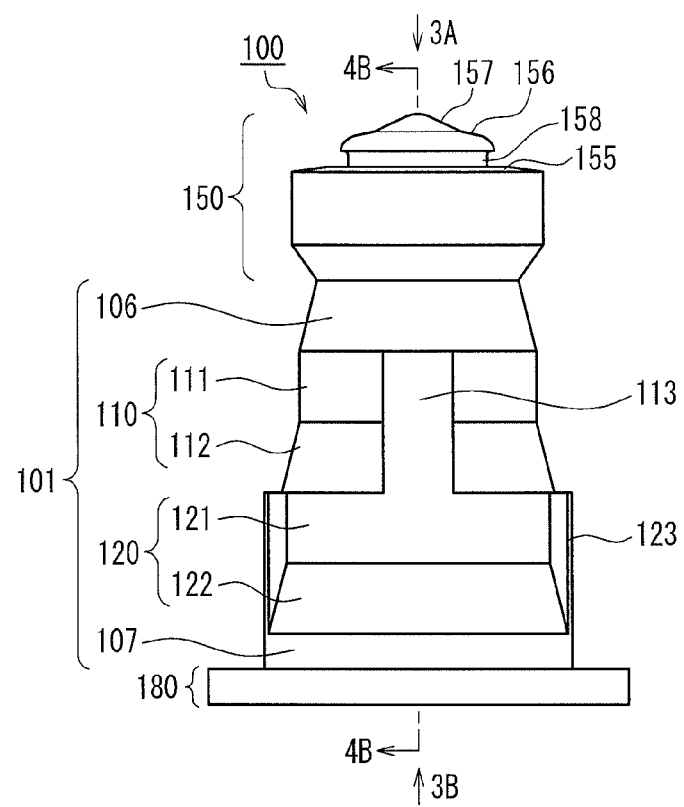
FIG. 2A is a front view of the cover for a male member according to Embodiment 1 of the present invention.
Figure 2B:
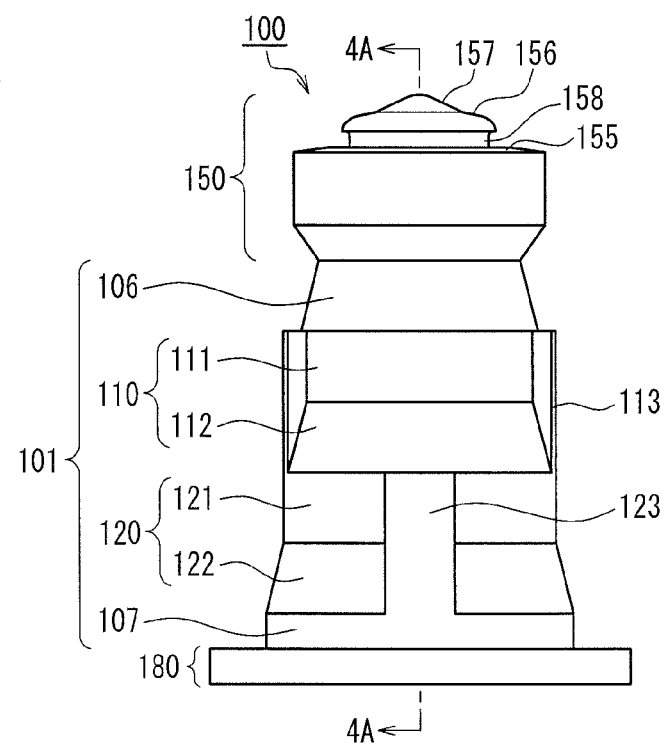
FIG. 2B is a side view of the same.
Figure 3A:
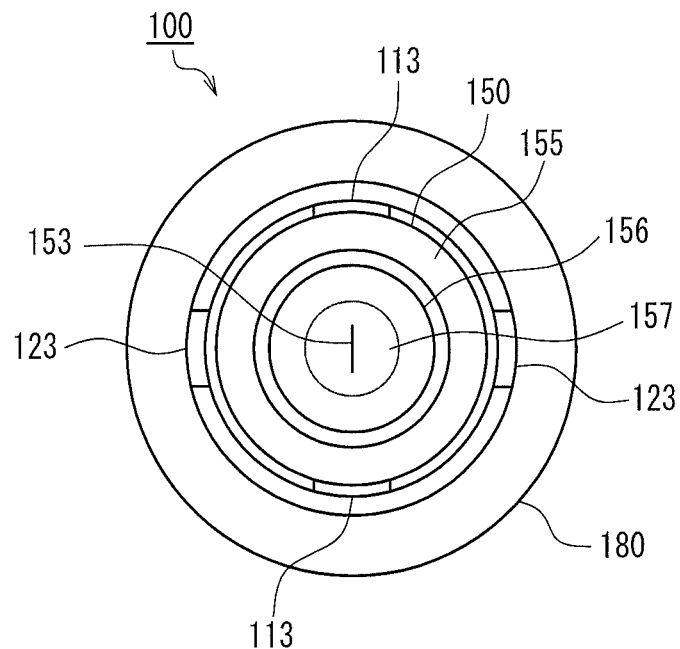
FIG. 3A is a plan view of the cover for a male member according to Embodiment 1 of the present invention as seen from an arrow 3A direction in FIG. 2A.
Figure 3B:
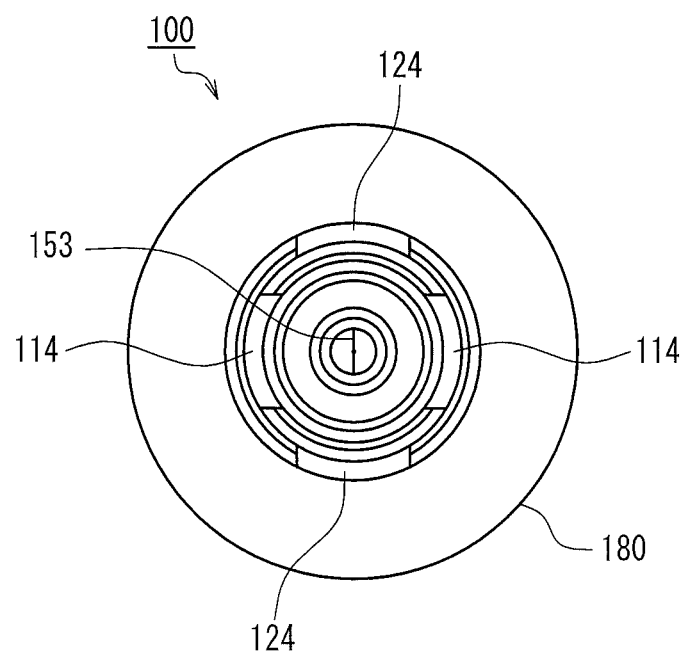
FIG. 3B is a bottom view of the cover for a male member according to Embodiment 1 of the present invention as seen from an arrow 3B direction in FIG. 2A.
Figure 4A:
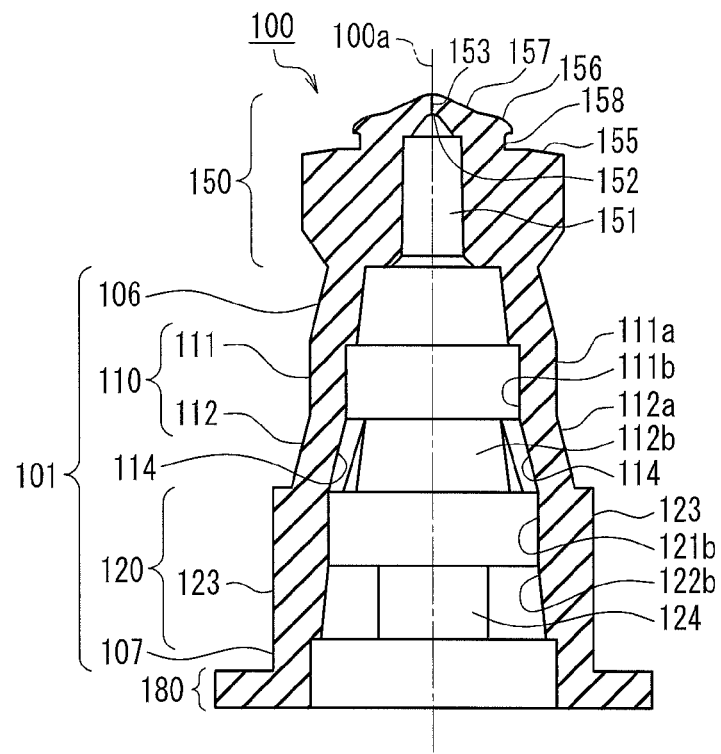
FIG. 4A is a cross-sectional view of the cover for a male member according to Embodiment 1 of the present invention taken along a plane including a line 4A-4A in FIG. 2B.
Figure 4B:
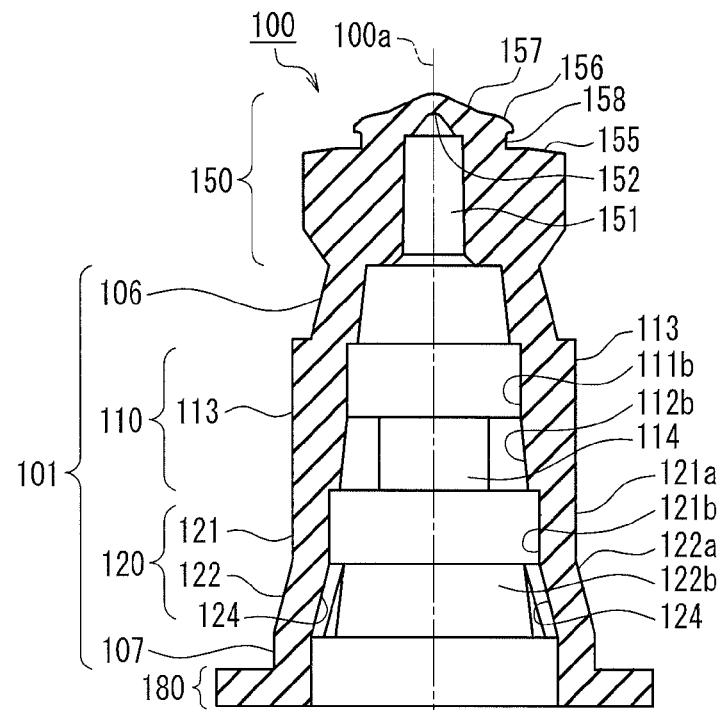
FIG. 4B is a cross-sectional view of the cover for a male member according to Embodiment 1 of the present invention taken along a plane including a line 4B-4B in FIG. 2A.

FIG. 1A is a perspective view of a cover for a male member (hereinafter referred to as simply a "cover") 100 according to Embodiment 1 of the present invention as seen from above, and FIG. 1B is a perspective view of the cover 100 as seen from below. FIG. 2A is a front view of the cover 100, FIG. 2B is a side view of the cover 100, FIG. 3A is a plan view of the cover 100 as seen from an arrow 3A direction in FIG. 2A, and FIG. 3B is a bottom view of the cover 100 as seen from an arrow 3B direction in FIG. 2A. Furthermore, FIG. 4A is a cross-sectional view of the cover 100 taken along a plane including a line 4A-4A in FIG. 2B, and FIG. 4B is a cross-sectional view of the cover 100 taken along a plane including a line 4B-4B in FIG. 2A.

The cover 100 includes an outer circumferential wall 101 that has a substantially tubular shape, a head portion 150 provided at one end of the outer circumferential wall 101, and a ring-shaped base portion 180 provided at the other end of the outer circumferential wall 101. The cover 100 can be formed integrally from a flexible (bendable) rubber-like elastic material (also called an elastomer, examples of which are silicone rubber and isoprene rubber). In FIGS. 4A and 4B, a dashed-dotted line 100a is the central axis of the cover 100. For the sake of convenience in the following description, the central axis 100a direction will be referred to as the "up-down direction" of the cover 100, the head portion 150 side will be referred to as the "upper side", and the base portion 180 side will be referred to as the "lower side". The direction along the plane orthogonal to the central axis 100a will be referred to as the "horizontal direction". Note that the "up-down direction" and the "horizontal direction" do not mean orientations during actual use of the cover 100. Also, the direction orthogonal to the central axis 100a will be referred to as the "radial direction", and the direction of rotation around the central axis 100a will be referred to as the "circumferential direction".

When compression force in the up-down direction (central axis 100a direction) is applied to the cover 100, the outer circumferential wall 101 undergoes elastic compression deformation such that its dimension in the up-down direction becomes shorter. The outer circumferential wall 101 includes a first compression unit 110 and a second compression unit 120 in the stated order from the head portion 150 side.

The first compression unit 110 will now be described.

The first compression unit 110 includes a first region 111 and a second region 112 in the stated order from the head portion 150 side, and these regions have differently-shaped outer faces (faces on the side opposite to the central axis 100a) and inner faces (faces opposing the central axis 100a).

As shown in FIGS. 4A and 4B, an outer face 111a of the first region 111 is a cylindrical face such that the outer diameter is constant in the central axis 100a direction. An inner face 111b of the first region 111 is also a cylindrical face such that the inner diameter is constant in the central axis 100a direction. Accordingly, the first region 111 of Embodiment 1 has a cylindrical shape with an outer face 111a and an inner face 111b that are both cylindrical faces.

As shown in FIGS. 4A and 4B, an outer face 112a of the second region 112 is a tapered face such that the outer diameter increases with increasing distance from the head portion 150 (in the present invention, this kind of tapered face is referred to as a "forward tapered face"). An inner face 112b of the second region 112 is also a tapered face such that the inner diameter increases with increasing distance from the head portion 150 (forward tapered face). Accordingly, the second region 112 of Embodiment 1 has a forward tapered shape with an outer face 112a and an inner face 112b that are both forward tapered faces.

A pair of protruding portions 113 that protrude outward in the radial direction are formed on the outer face of the first compression unit 110 at symmetric positions with respect to the central axis 100a. The protruding portions 113 are rib-shaped protrusions that extend along a direction parallel to the central axis 100a. The outer faces of the protruding portions 113 (faces on the side opposite to the central axis 100a) are cylindrical faces whose central axis is the central axis 100a. The protruding portions 113 extend from the upper end to the lower end of the first compression unit 110 over the entire range of the central axis 100a direction of the first compression unit 110.

Figure 5A:
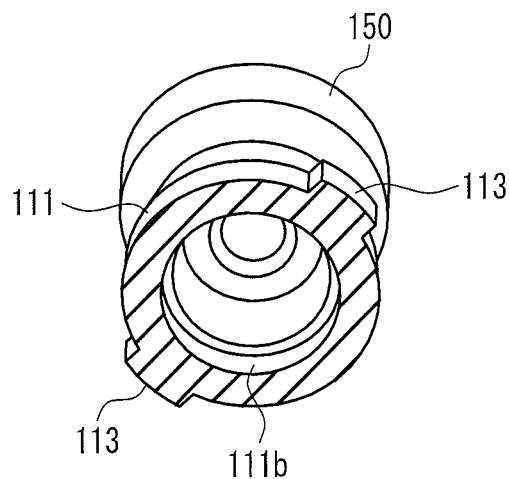
FIG. 5A is a perspective view of the cover for a male member according to Embodiment 1 of the present invention cut along a horizontal plane that passes through a first region of a first compression unit, as seen from below.
Figure 5B:
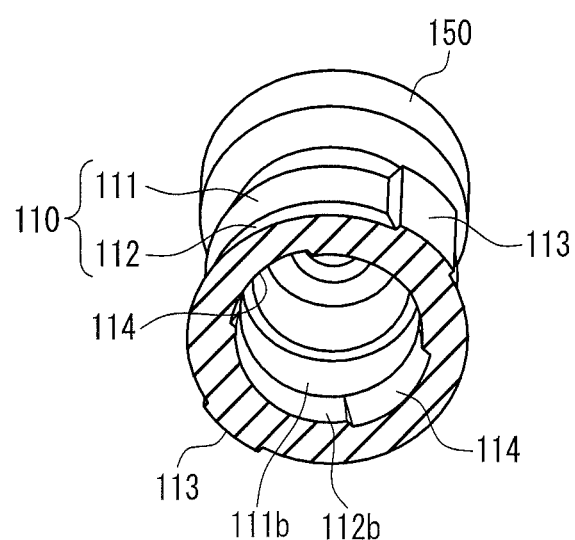
FIG. 5B is a perspective view of the cover for a male member according to Embodiment 1 of the present invention cut along a horizontal plane that passes through a second region of the first compression unit, as seen from below.

FIG. 5A is a perspective view of the cover 100 cut along a horizontal plane (plane orthogonal to the central axis 100a) that passes through the first region 111 of the first compression unit 110, as seen from below. FIG. 5B is a perspective view of the cover 100 cut along a horizontal plane that passes through the second region 112 of the first compression unit 110, as seen from below. As is shown most clearly in FIG. 5B, a pair of receding portions 114 whose diameters increase outward in the radial direction are formed in the inner face 112b of the second region 112 at symmetric positions with respect to the central axis 100a. The receding portions 114 are groove-shaped recessions that extend along a direction parallel to the central axis 100a. The bottom faces of the receding portions 114 (faces opposing the central axis 100a) are conical faces whose central axis is the central axis 100a. The receding portions 114 extend from the upper end to the lower end of the second region 112 over the entire range of the central axis 100a direction of the second region 112. In a view along a direction parallel to the central axis 100a, the direction in which the pair of receding portions 114 oppose each other is orthogonal to the direction in which the pair of protruding portions 113 oppose each other.

Due to the protruding portions 113 and the receding portions 114 being formed so as to alternate at equiangular intervals in the circumferential direction of the first compression unit 110 as described above, the thickness of the first compression unit 110 (dimension in the direction orthogonal to the central axis 100a) periodically changes in the circumferential direction. More specifically, the first region 111 has a constant thickness (basic thickness) in the region other than the protruding portions 113, and has a thickness greater than the basic thickness in the protruding portions 113 (see FIG. 5A). Also, the second region 112 has a constant thickness (basic thickness) in the region other than the protruding portions 113 and the receding portions 114, a thickness greater than the basic thickness in the protruding portions 113, and a thickness lower than the basic thickness in the receding portions 114 (see FIG. 5B). In the first compression unit 110, the protruding portions 113 configure thick portions that have a locally increased thickness, and the receding portions 114 configure thin portions that have a locally reduced thickness.

The second compression unit 120 will now be described.

The second compression unit 120 includes a first region 121 and a second region 122 in the stated order from the head portion 150 side, and these regions have differently-shaped outer faces (faces on the side opposite to the central axis 100a) and inner faces (faces opposing the central axis 100a).

As shown in FIGS. 4A and 4B, an outer face 121a of the first region 121 is a cylindrical face such that the outer diameter is constant in the central axis 100a direction. An inner face 121b of the first region 121 is also a cylindrical face such that the inner diameter is constant in the central axis 100a direction. Accordingly, the first region 121 of Embodiment 1 has a cylindrical shape with an outer face 121a and an inner face 121b that are both cylindrical faces.

As shown in FIGS. 4A and 4B, an outer face 122a of the second region 122 is a tapered face such that the outer diameter increases with increasing distance from the head portion 150 (forward tapered face). An inner face 122b of the second region 122 is also a tapered face such that the inner diameter increases with increasing distance from the head portion 150 (forward tapered face). Accordingly, the second region 122 of Embodiment 1 has a forward tapered shape with an outer face 122a and an inner face 122b that are both forward tapered faces.

A pair of protruding portions 123 that protrude outward in the radial direction are formed on the outer face of the second compression unit 120 at symmetric positions with respect to the central axis 100a. The protruding portions 123 are rib-shaped protrusions that extend along a direction parallel to the central axis 100a. The outer faces of the protruding portions 123 (faces on the side opposite to the central axis 100a) are cylindrical faces whose central axis is the central axis 100a. The protruding portions 123 extend from the upper end to the lower end of the second compression unit 120 over the entire range of the central axis 100*a* direction of the second compression unit 120.

Figure 5C:
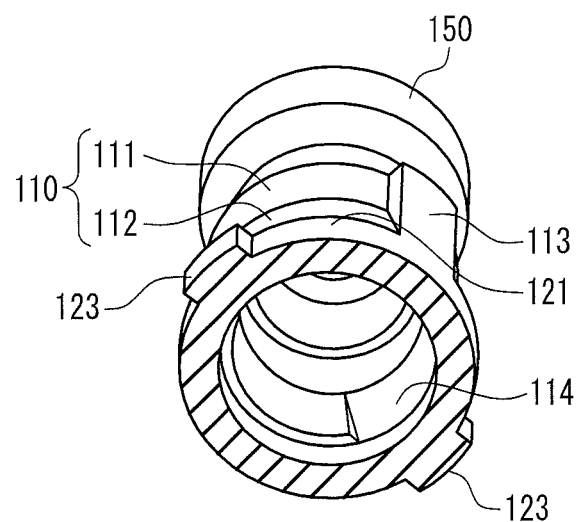
FIG. 5C is a perspective view of the cover for a male member according to Embodiment 1 of the present invention cut along a horizontal plane that passes through a first region of a second compression unit, as seen from below.
Figure 5D:
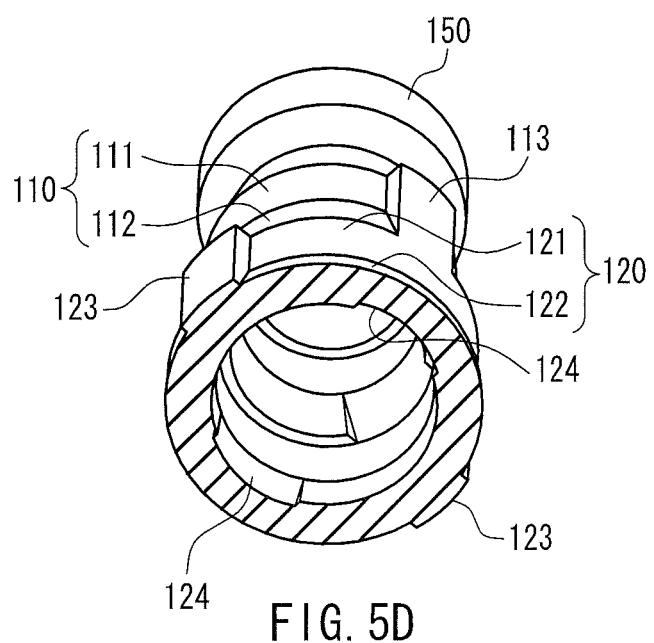
FIG. 5D is a perspective view of the cover for a male member according to Embodiment 1 of the present invention cut along a horizontal plane that passes through a second region of the second compression unit, as seen from below.

FIG. 5C is a perspective view of the cover 100 cut along a horizontal plane (plane orthogonal to the central axis 100*a*) that passes through the first region 121 of the second compression unit 120, as seen from below. FIG. 5D is a perspective view of the cover 100 cut along a horizontal plane that passes through the second region 122 of the second compression unit 120, as seen from below. As is shown most clearly in FIG. 5D, a pair of receding portions 124 whose diameters increase outward in the radial direction are formed in the inner face 122*b* of the second region 122 at symmetric positions with respect to the central axis 100*a*. The receding portions 124 are groove-shaped recessions that extend along a direction parallel to the central axis 100*a*. The bottom faces of the receding portions 124 (faces opposing the central axis 100*a*) are conical faces whose central axis is the central axis 100*a*. The receding portions 124 extend from the upper end to the lower end of the second region 122 over the entire range of the central axis 100*a* direction of the second region 122. In a view along a direction parallel to the central axis 100*a*, the direction in which the pair of receding portions 124 oppose each other is orthogonal to the direction in which the pair of protruding portions 123 oppose each other.

Due to the protruding portions 123 and the receding portions 124 being formed so as to alternate at equiangular intervals in the circumferential direction of the second compression unit 120 as described above, the thickness of the second compression unit 120 (dimension in the direction orthogonal to the central axis 100*a*) periodically changes in the circumferential direction. More specifically, the first region 121 has a constant thickness (basic thickness) in the region other than the protruding portions 123, and has a thickness greater than the basic thickness in the protruding portions 123 (see FIG. 5C). Also, the second region 122 has a constant thickness (basic thickness) in the region other than the protruding portions 123 and the receding portions 124, a thickness greater than the basic thickness in the protruding portions 123, and a thickness lower than the basic thickness in the receding portions 124 (see FIG. 5D). In the second compression unit 120, the protruding portions 123 configure thick portions that have a locally increased thickness, and the receding portions 124 configure thin portions that have a locally reduced thickness.

As described above, considering the first compression unit 110 and the second compression unit 120 that are neighboring to each other, the second compression unit 120 has a relatively large diameter (dimension), but their shapes are substantially the same. Note that the phase of periodic change in thickness along the circumferential direction is shifted by 90 degrees between the first compression unit 110 and the second compression unit 120. Specifically, in a view along a direction parallel to the central axis 100*a*, the positions of the pair of thick portions of the first compression unit 110 (i.e., the pair of protruding portions 113) and the positions of the pair of thick portions of the second compression unit 120 (i.e., the pair of protruding portions 123) differ by 90 degrees with respect to the central axis 100*a*. Also, in a view along a direction parallel to the central axis 100*a*, the positions of the pair of thin portions of the first compression unit 110 (i.e., the pair of receding portions 114) and the positions of the pair of thin portions of the second compression unit 120 (i.e., the pair of receding portions 124) differ by 90 degrees with respect to the central axis 100*a*.

A first connecting portion 106 is provided between the head portion 150 and the first compression unit 110. The first connecting portion 106 has a forward tapered shape with an inner face and an outer face that are tapered faces that increase in size with increasing distance from the head portion 150 (forward tapered faces).

A second connecting portion 107 is provided between the base portion 180 and the second compression unit 120. The second connecting portion 107 has a cylindrical shape with an inner face and an outer face that are both cylindrical faces.

Note that the shapes of the first connecting portion 106 and the second connecting portion 107 are not limited to the above description, and may be any shape. Also, one or both of the first connecting portion 106 and the second connecting portion 107 may be omitted.

As shown in FIGS. 4A and 4B, an inner cavity 151 that is in communication with the space inside the outer circumferential wall 101 is formed in the head portion 150. The tip of the male member is inserted into the inner cavity 151 (see FIG. 6 described later). The inner circumferential face of the inner cavity 151 may have any shape, and it can be set to a cylindrical face or a conical face whose inner diameter decreases with increasing distance from the outer circumferential wall 101 (tapered face). It is preferable that the inner circumferential face of the inner cavity 151 is a shape that comes into close contact with the tip of the male member so as to block the opening of the flow channel through which liquid in the male member flows. A slit 153 that passes through the head portion 151 in the up-down direction is formed at a deepest portion 152 of the inner cavity 151. As shown in FIG. 3A, the slit 153 is a linear incision that is shaped as the character "–" (minus) when viewed from above. It is preferable that the mutually-opposing edges that form the slit 153 are in contact with each other in the normal state in which the male member does not pass through the slit 153.

As shown in FIG. 1A, an apex portion 156 that protrudes from an upper face 155 of the head portion 150 in the shape of a mushroom is formed on the upper face 155. The tip of the apex portion 156 is a convex curved face 157 that smoothly bulges in the shape of a dome, such as a spherical face. A neck portion 158 is formed between the convex curved face 157 and the upper face 155 of the head portion 150. The outer diameter of the neck portion 158 is smaller than the maximum outer diameter of the apex portion 156. In a view from above (see FIG. 3A), the slit 153 is formed in the center of the convex curved face 157.

The base portion 180 is provided in order to fix the cover 100. There are no particular limitations on the method of fixing the cover 100 using the base portion 180, and any method can be used, such as adhesion, fusion, engagement, or mating. The shape of the base portion 180 can be set to any shape in accordance with the method of fixing. In order to accurately position the cover 100, the base portion 180 may be formed into a mating shape for mating with a partner member for fixing the cover 100.

Figure 6:
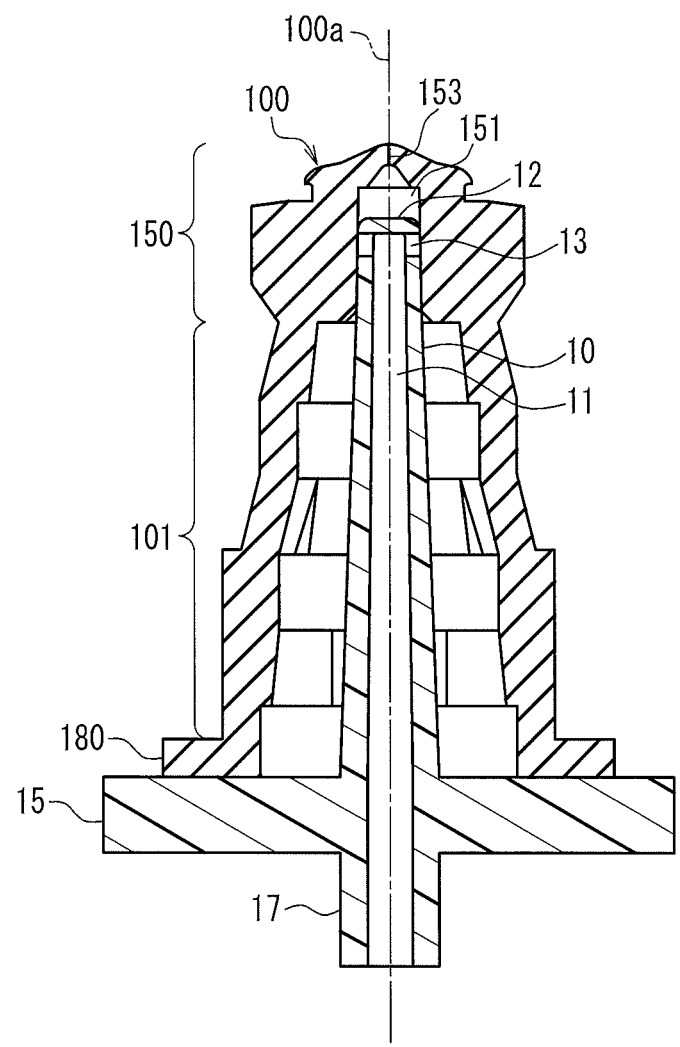
FIG. 6 is a cross-sectional view of the cover for a male member according to Embodiment 1 of the present invention in a state of being attached to a male luer.

FIG. 6 is a cross-sectional view of the cover 100 in a state of being attached to a male luer (male member) 10. The cross-section in FIG. 6 is the same as the cross-section in FIG. 4A. The male luer 10 has bar shape in which a flow channel 11 for the flow of a liquid is formed in the lengthwise direction. The central axis 100*a* of the cover 110 coincides with the central axis of the male luer 10. The outer circumferential face (side face) of the male luer 10 is a tapered face such that the outer diameter decreases with decreasing distance from a tip 12. Note that the shape of the outer circumferential face of the male luer 10 is not limited to this, and it may be a cylindrical face such that the outer diameter is constant along the lengthwise direction of the male luer 10, for example. A transverse hole 13 is formed at a position in the vicinity of the tip 12 of the outer circumferential face of the male luer 10. The transverse hole 13 is a through-hole that is in communication with the flow channel 11 and passes through the male luer 10 in a direction that is substantially orthogonal to the lengthwise direction of the male luer 10 (in the diameter direction). In the present embodiment, a pair of transverse holes 13 are formed along the diameter direction of the male luer 10, but the number of transverse holes 13 is not limited to this, and one or three or more may be formed. A liquid flows out of the flow channel 11 and flows into the flow channel 11 through the transverse holes 13. As shown in FIG. 6, when the tip 12 of the male luer 10 has been inserted into the inner cavity 151 of the head portion 150 of the cover 100, the inner face of the inner cavity 151 is in close contact with the outer face of the tip 12 of the male luer 10, and the transverse holes 13 are blocked.

The male luer 10 protrudes from a base 15. The base portion 180 of the cover 100 is fixed to the base 15. A tubular portion 17 that is in communication with the male luer 10 and has a substantially cylindrical shape is formed on the side of the base 15 opposite to the male luer 10. In order to transport a liquid to the male luer 10, a tube (not shown) that is bendable, for example, is connected to the tubular portion 17. It is preferable that the male luer 10 is made of a hard material that can be considered virtually to be a rigid body. Specifically, the male luer 10 can be created with a method of, for example, integral formation with the base 15 and the tubular portion 17 using a resin material such as polyacetal or polycarbonate.

The configurations of the male luer 10, the base 15, and the tubular portion 17 are not limited to the configurations in FIG. 6. For example, the transverse holes 13 may be omitted, and the flow channel 11 may be formed so as to open toward the slit 153 of the cover 100, as with the opening 912 in the male luer 910 in FIG. 19. Note that it is preferable that the transverse holes 13 are formed in the outer circumferential face in the vicinity of the tip 12 as shown in FIG. 6, so that the transverse holes 13 can be blocked reliably by the inner face of the inner cavity 151 of the cover 100. Also, the tubular portion 17 may be omitted, and the male luer 10 and the base 15 may be integrated with a member that constitutes a male connector.

The following describes effects of the cover 100 of Embodiment 1 configured as described above, by way of a comparison with a cover for a male member 500 according to a comparative example.

Figure 7A:
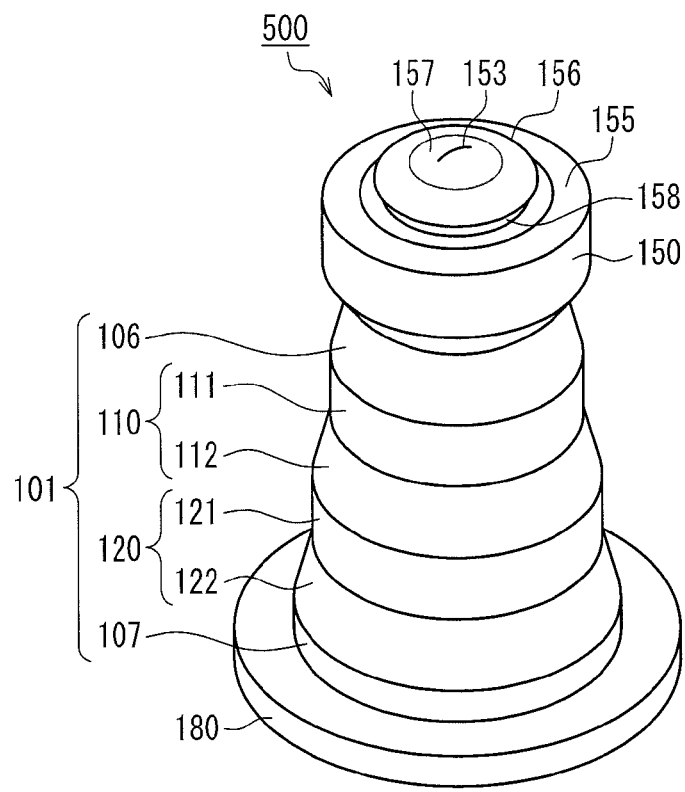
FIG. 7A is a perspective view of a cover for a male member according to a comparative example as seen from above.
Figure 7B:
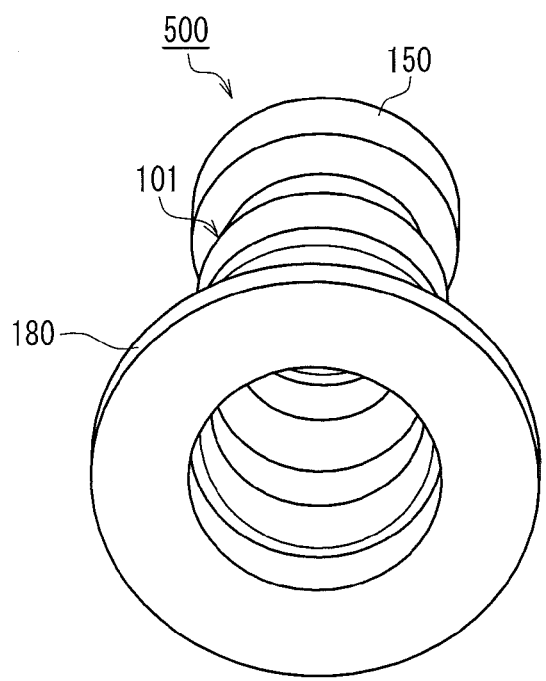
FIG. 7B is a perspective view of the same as seen from below.

FIG. 7A is a perspective view of the cover 500 according to the comparative example as seen from above, and FIG. 7B is a perspective view of the cover 500 as seen from below. The cover 500 is different from the above-described cover 100 of Embodiment 1 in that the protruding portions 113 and 123 and the receding portions 114 and 124 are not formed. Accordingly, in the cover 500 of the comparative example, the thicknesses of the first compression unit 110 and the second compression unit 120 are constant in the circumferential direction. In FIGS. 7A and 7B, constituent elements that correspond to constituent elements of the cover 100 of Embodiment 1 have been given the same reference signs.

The following two experiments were carried out using the cover 100 of Embodiment 1 and the cover 500 of the comparative example.

Experiment 1

Figure 19:
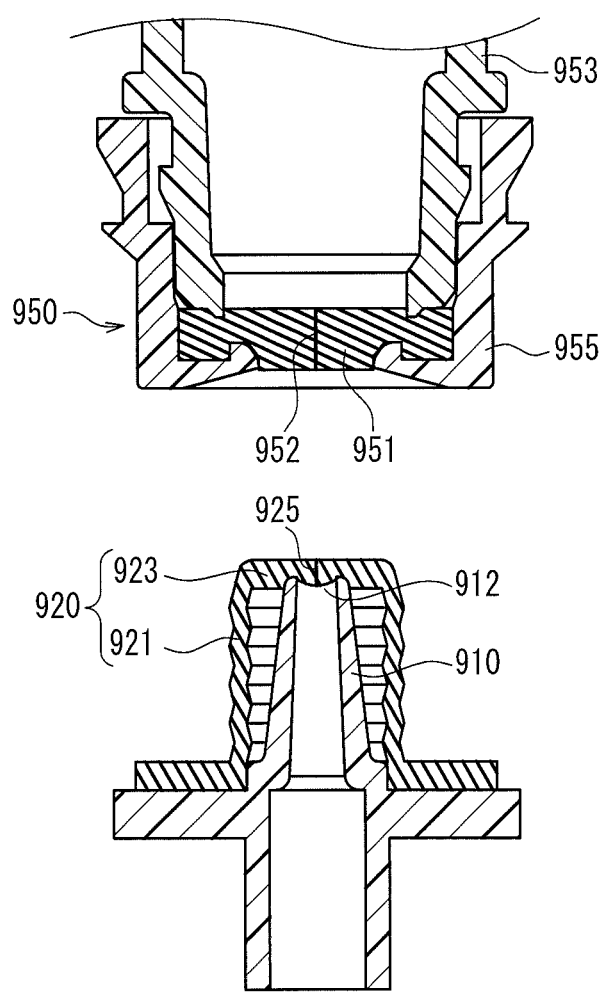
FIG. 19 is a cross-sectional view showing a cover attached to a male luer that is to be connected to a needleless port.

In Experiment 1, male luers 10 shown in FIG. 6 with the covers 100 and 500 attached were connected to the needleless port 950 (see FIG. 19). Aspects of the deformation of the covers 100 and 500 in the state before connection and the connected state were then observed by capturing cross-sectional images using X-ray CT.

FIGS. 8A and 8B are cross-sectional views showing the state before the male luer 10 having the cover 100 of Embodiment 1 attached thereto is connected to the needleless port 950. The cross-sections in FIGS. 8A and 8B are the same as the cross-sections in FIGS. 4A and 4B respectively.

FIGS. 9A and 9B are cross-sectional views showing the state where the male luer 10 having the cover 100 of Embodiment 1 attached thereto has been connected to the needleless port 950. The cross-sections in FIGS. 9A and 9B are the same as the cross-sections in FIGS. 8A and 8B respectively.

As shown in FIGS. 9A and 9B, the male luer 10 has passed through the slit 153 formed in the head portion 150 of the cover 100, and furthermore has passed through the slit 952 in the septum 951 of the needleless port 950. On the other hand, the cover 100 has received compression force from the port cap 955 of the needleless port 950, and the outer circumferential wall 101 of the cover 100 has undergone a large amount of compression deformation. In both of FIGS. 9A and 9B, the deformed shapes of the outer circumferential wall 101 are substantially symmetrical with respect to the central axis 100a. This shows that the outer circumferential wall 101 has undergone virtually no buckling deformation.

As can be understood by comparing FIGS. 9A and 9B, the deformation of the outer circumferential wall 101 is not constant in the circumferential direction. Specifically, regarding the first compression unit 110, in the cross-section including the pair of receding portions 114 (thin portions), the first compression unit 110 undergoes a large amount of bending deformation so that the outer face 111a and the outer face 112a come into contact each other as shown in FIG. 9A, whereas in the cross-section including the pair of protruding portions 113 (thick portions), the first compression unit 110 bends slightly so as to bulge outward as shown in FIG. 9B. Also, regarding the second compression unit 120, in the cross-section including the pair of receding portions 124 (thin portions), the second compression unit 120 undergoes a large amount of bending deformation so that the outer face 121a and the outer face 122a come into contact each other as shown in FIG. 9B, whereas in the cross-section including the pair of protruding portions 123 (thick portions), the second compression unit 120 bends slightly so as to bulge outward as shown in FIG. 9A. In this way, the first compression unit 110 and the second compression unit 120 undergo almost no deformation in the portions that have a relatively high mechanical strength (rigidity) due to the formation of the thick portions (protruding portions 113 and 123), and undergo a large amount of bending deformation in the portions that have a relatively low mechanical strength (rigidity) due to the formation of the thin portions (receding portions 114 and 124). Also, the positions of the portions provided with the thick portions and the thin portions differ by 90 degrees around the central axis 100a between the first compression unit 110 and the second compression unit 120, and therefore in the cross-section shown in FIG. 9A, mainly the first compression unit 110 undergoes deformation with almost no deformation of the second compression unit 120, and in the cross-section shown in FIG. 9B, mainly the second compression unit 120 undergoes deformation with almost no deformation of the first compression unit 110. As a result, the outer circumferential wall 101 can undergo a large amount of compression deformation in the central axis 100a direction without undergoing buckling deformation.

Since the first compression unit 110 and the second compression unit 120 have substantially similar shapes, the first compression unit 110 and the second compression unit 120 have a common mode of deformation in which portions having a large amount of change in dimension in the central axis 100a direction (portions having a relatively low mechanical strength) and portions having a small amount of change in dimension in the central axis 100a direction (portions having a relatively high mechanical strength) are formed so as to alternate in the circumferential direction. Since such a first compression unit 110 and second compression unit 120 are stacked in the up-down direction with shifted phases, it is possible to increase the amount of change in dimension of the cover 100 overall due to compression, while also suppressing buckling deformation. Moreover, since the diameter of the second compression unit 120 is larger than that of the first compression unit 110, the outer circumferential wall 101 can undergo deformation such that the first compression unit 110 enters the second compression unit 120. This enables further increases in the amount of change in dimension of the cover 100. Increasing the amount of change in dimension of the cover 100 enables the height of the cover 100 (dimension in the central axis 100a direction) during compression (FIGS. 9A and 9B) to be reduced, thus making it possible to increase the depth of insertion of the male luer 10 into the needleless port 950.

FIGS. 10A and 10B are cross-sectional views showing the state before the male luer 10 having the cover 500 of the comparative example attached thereto is connected to the needleless port 950. FIG. 10B is a cross-sectional view taken along a plane orthogonal to the cross-section in FIG. 10A.

FIGS. 11A and 11B are cross-sectional views showing the state where the male luer 10 having the cover 500 of the comparative example attached thereto has been connected to the needleless port 950. The cross-sections in FIGS. 11A and 11B are the same as the cross-sections in FIGS. 10A and 10B respectively.

The depths of insertion of the male luer 10 into the needleless port 950 in FIGS. 11A and 11B are the same as those in FIGS. 9A and 9B of Embodiment 1. Accordingly, the amounts of change in dimension in the central axis 100a direction of the cover 500 are the same as those of the cover 100 in FIGS. 9A and 9B. However, the deformed shapes of the outer circumferential wall 101 of the cover 500 shown in FIGS. 11A and 11B are greatly different from those of the outer circumferential wall 101 of the cover 100 shown in FIGS. 9A and 9B. Moreover, whereas the deformed shape of the outer circumferential wall 101 is substantially symmetrical with respect to the central axis 100a in FIG. 11A, it is clearly asymmetrical with respect to the central axis 100a in FIG. 11B. This shows that the outer circumferential wall 101 has undergone buckling deformation in the cross-section in FIG. 11B.

In the cover 500 of the comparative example, the thickness of the outer circumferential wall 101 is constant in the circumferential direction, and therefore the mechanical strength (rigidity) of the outer circumferential wall 101 is also constant in the circumferential direction. Accordingly, in a case such as where the direction of the compression force applied to the cover 500 is slightly inclined with respect to the central axis 100a of the cover 500, buckling deformation easily occurs as shown in FIG. 11B.

Although the male luer 10 having the cover 500 of the comparative example attached thereto was repeatedly inserted into and withdrawn from the needleless port 950, it was not possible to insert the male luer 10 into the needleless port 950 without causing the cover 500 to undergo buckling deformation.

Experiment 2

Change in compressive load in the process of compressing the covers 100 and 500 used in Experiment 1 and then returning them (allowing them to extend) to their original state was measured.

Figure 12:
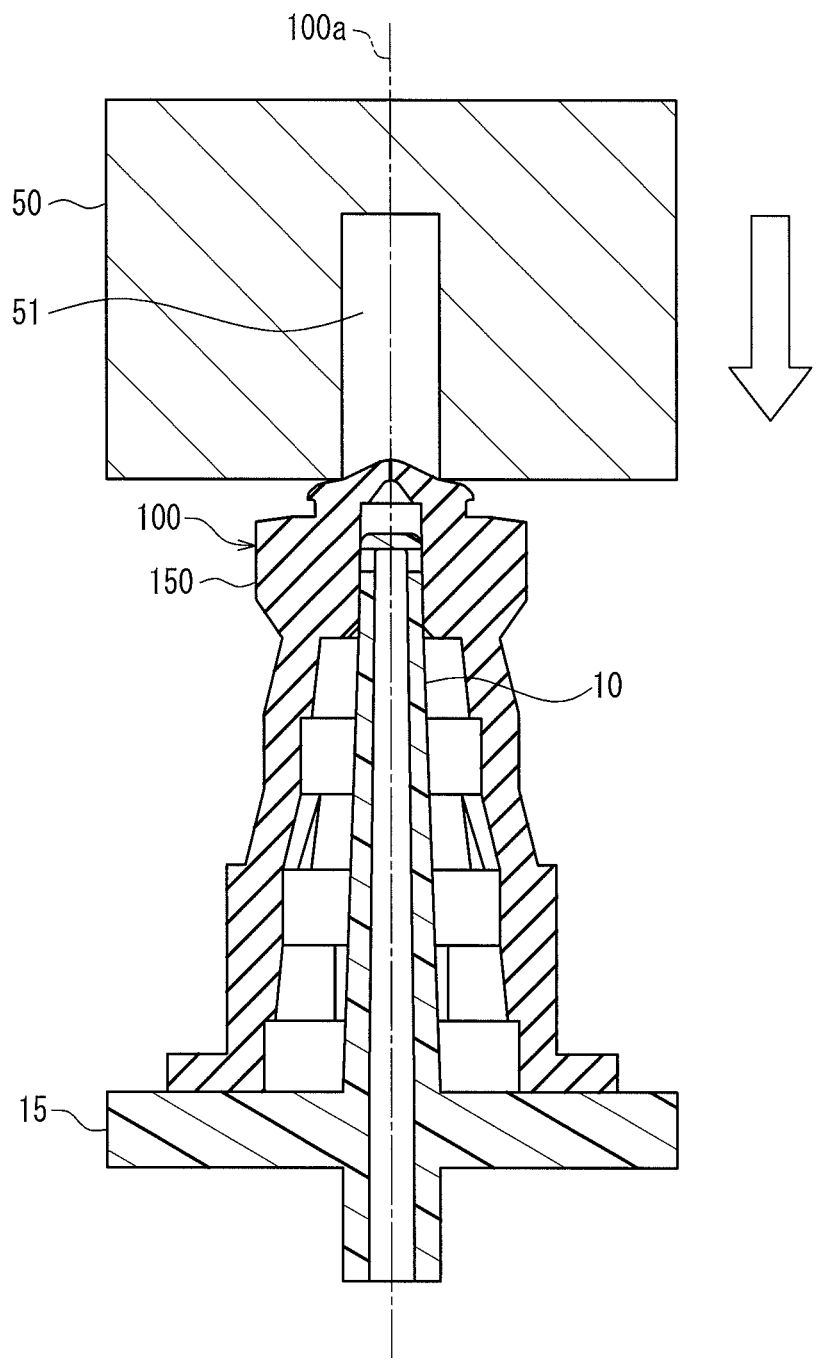
FIG. 12 is a cross-sectional view for describing the method of Experiment 2 regarding the cover for a male member according to Embodiment 1 of the present invention in a state of being attached to a male luer.

FIG. 12 is a cross-sectional view for describing the method of Experiment 2 regarding the cover 100. Similarly to Experiment 1, the cover 100 was attached to a male luer 10. The base 15 of the male luer 10 was held such that the central axis 100a of the cover 100 was vertical. A compression block 50 provided with a hole 51 that can receive insertion of the male luer 10 was attached to an elevating apparatus (not shown) above the cover 100. As shown in FIG. 12, the position at which the edge of the opening of the hole 51 comes into contact with the head portion 150 of the cover 100 was set as the initial position of the compression block 50. The compression block 50 then was lowered from the initial position and thereafter raised to the initial position. The repulsive force applied to the compression block 50 by the cover 100 (i.e., the compressive load for compressing the cover 100) in the process of this raising and lowering performed by the compression block 50 was measured. The speed of the compression block 50 was 200 mm/min during both the lowering and the raising, and the distance (stroke) from the initial position of the compression block 50 to the lowest position was set to 6 mm. The amount of change in dimension of the cover 100 when the compression block 50 was at the lowest position was substantially the same as that in the state shown in FIGS. 9A and 9B in Experiment 1. Considering the lowering and the raising of the compression block 50 to be one cycle, five cycles were performed consecutively for each sample. This was carried out for three samples.

Similar measurement was also carried out for the cover 500 of the comparative example used in Experiment 1.

Figure 13:
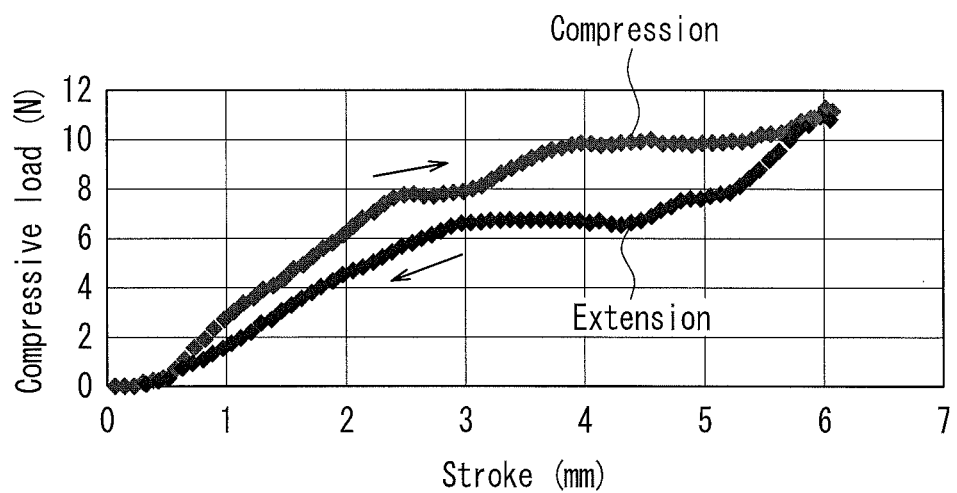
FIG. 13 is a graph showing measurement results in Experiment 2 regarding the cover for a male member according to Embodiment 1 of the present invention in a state of being attached to the male luer.
Figure 14:
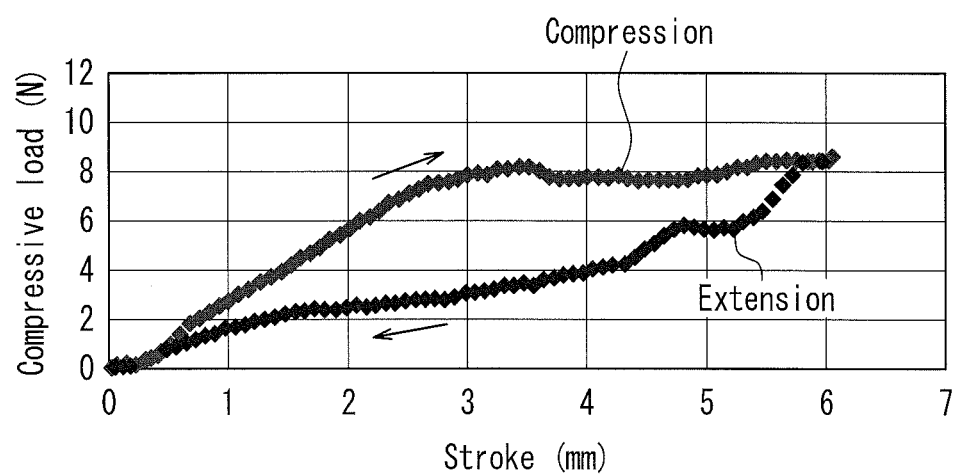
FIG. 14 is a graph showing measurement results in Experiment 2 regarding a cover for a male member according to the comparative example in a state of being attached to a male luer.

FIG. 13 is a graph showing change in compressive load in a representative cycle regarding the cover 100 of Embodiment 1, and FIG. 14 is a graph showing change in compressive load in a representative cycle regarding the cover 500 of the comparative example.

As can be understood by comparing FIGS. 13 and 14, the compressive load at the maximum stroke is higher with the cover 100 of Embodiment 1 (FIG. 13) than with the cover 500 of the comparative example (FIG. 14). Also, the difference in the compressive load between the compression process and the extension process is smaller with the cover 100 of Embodiment 1 (FIG. 13) than with the cover 500 of the comparative example (FIG. 14). This difference between the cover 100 and the cover 500 is thought to be due to the difference in whether or not the outer circumferential wall 101 undergoes buckling deformation during compression as described in Experiment 1. In other words, since the outer circumferential wall 101 of the cover 500 of the comparative example undergoes buckling deformation, the repulsive force generated when the cover 500 is compressed at the maximum stroke is small. Also, some of the energy applied for causing the cover 500 of the comparative example to undergo compression deformation is consumed by the buckling deformation of the outer circumferential wall 101, and therefore the difference in compressive load between the compression process and the extension process is high.

Accordingly, if there is a large amount of frictional force between the outer circumferential face of the male luer 10 and the edges of the slit 153 in the head portion 150, the cover 500 of the comparative example can be in a situation in which the compressed cover 500 does not return to its original state by extending due to its elastic restoring force. There is a low possibility of this situation occurring with the cover 100 of Embodiment 1.

Embodiment 2

Figure 15:
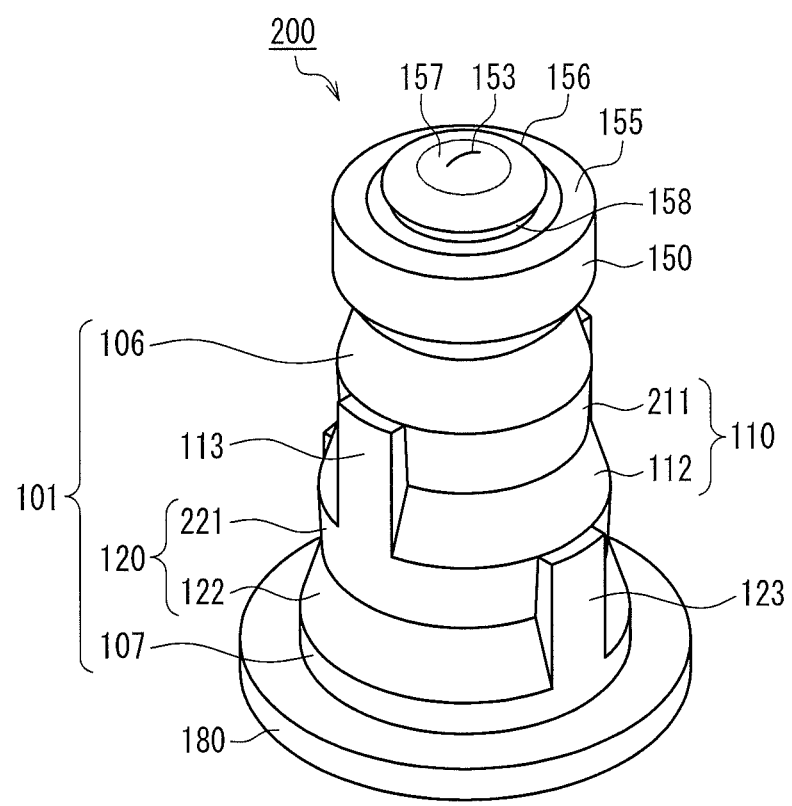
FIG. 15 is a perspective view of a cover for a male member according to Embodiment 2 of the present invention as seen from above.
Figure 16A:
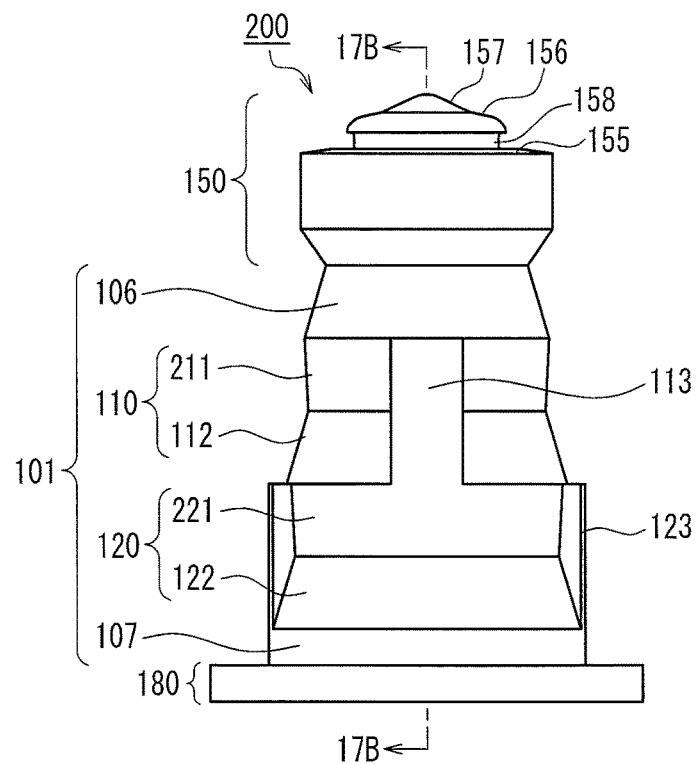
FIG. 16A is a front view of the cover for a male member according to Embodiment 2 of the present invention.
Figure 16B:
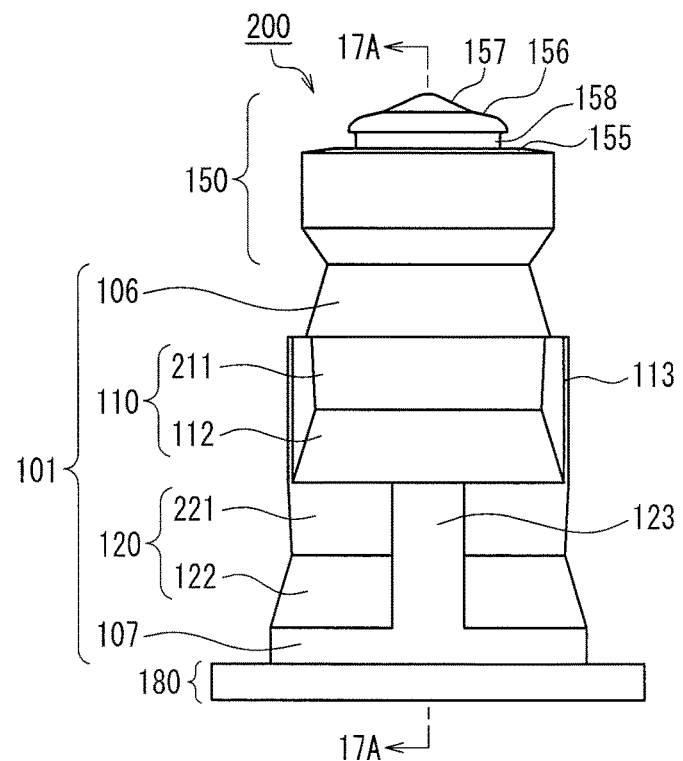
FIG. 16B is a side view of the same.
Figure 17A:
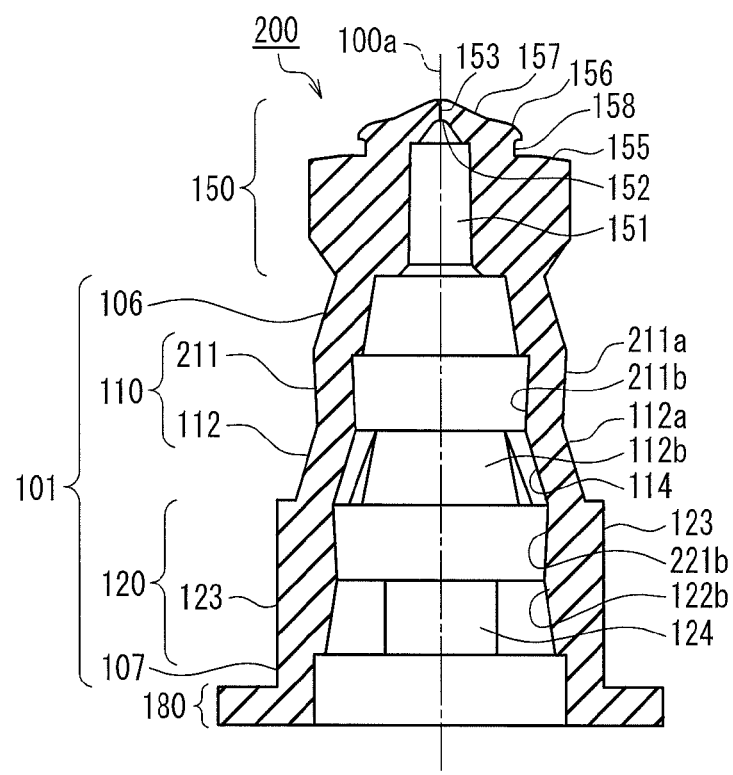
FIG. 17A is a cross-sectional view of the cover for a male member according to Embodiment 2 of the present invention taken along a plane including a line 17A-17A in FIG. 16B.
Figure 17B:
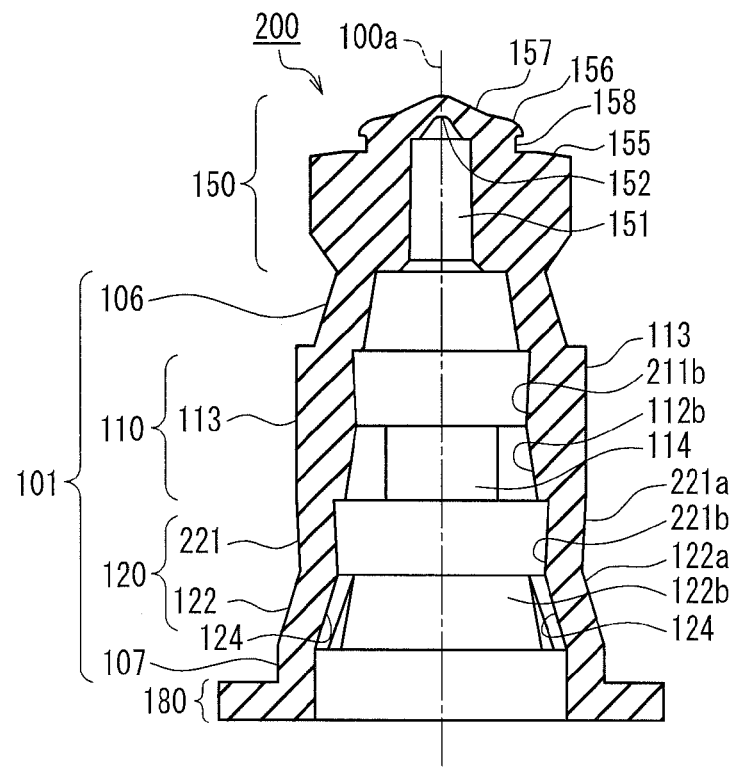
FIG. 17B is a cross-sectional view of the cover for a male member according to Embodiment 2 of the present invention taken along a plane including a line 16B-16B in FIG. 16A.

FIG. 15 is a perspective view of a cover for a male member (hereinafter referred to as simply a "cover") 200 according to Embodiment 2 of the present invention as seen from above, FIG. 16A is a front view of the cover 200, and FIG. 16B is a side view of the cover 200. FIG. 17A is a cross-sectional view of the cover 200 taken along a plane including a line 17A-17A in FIG. 16B, and FIG. 17B is a cross-sectional view of the cover 200 taken along a plane including a line 17B-17B in FIG. 16A. In these figures, members that are the same as in Embodiment 1 have been given the same reference signs. The following description of Embodiment 2 focuses on the differences from Embodiment 1.

In Embodiment 2, an outer face 211a of a first region 211 of the first compression unit 110 is a tapered face such that the outer diameter decreases with increasing distance from the head portion 150 (in the present invention, this kind of tapered face is referred to as a "reverse tapered face"). An inner face 211b of the first region 211 is also a tapered face such that the inner diameter decreases with increasing distance from the head portion 150 (reverse tapered face). Accordingly, the first region 211 of Embodiment 2 has a reverse tapered shape with an outer face 211a and an inner face 211b that are both reverse tapered faces.

Also, an outer face 221a of a first region 221 of the second compression unit 120 is a tapered face such that the outer diameter decreases with increasing distance from the head portion 150 (reverse tapered face). An inner face 221b of the first region 221 is also a tapered face such that the inner diameter decreases with increasing distance from the head portion 150 (reverse tapered face). Accordingly, the first region 221 of Embodiment 2 also has a reverse tapered shape with an outer face 221a and an inner face 221b that are both reverse tapered faces.

Embodiment 2 is the same as Embodiment 1 described above, with the exception of the above-described content.

In Embodiment 2, the first region 211 configuring the first compression unit 110 has a reverse tapered shape, and the second region 112 therebelow has a forward tapered shape. The first region 211 and the second region 112 are joined substantially in the shape of a "<" in a cross-section taken along a plane including the central axis 100a. Accordingly, when compression force in the up-down direction is applied, the portions of the first compression unit 110 that have a relatively low mechanical strength (rigidity) reliably can be caused to undergo bending deformation such that the outer face 211a and the outer face 112a come into contact similarly to the state described with reference to FIG. 9A.

Similarly, the first region 221 configuring the second compression unit 120 has a reverse tapered shape, and the second region 122 therebelow has a forward tapered shape. The first region 221 and the second region 122 are joined substantially in the shape of a "<" in a cross-section taken along a plane including the central axis 100a. Accordingly, when compression force in the up-down direction is applied, the portions of the second compression unit 120 that have a relatively low mechanical strength (rigidity) reliably can be caused to undergo bending deformation such that the outer face 221a and the outer face 122a come into contact similarly to the state described with reference to FIG. 9B.

In this way, the compression units 110 and 120 of Embodiment 2 are configured by a reverse tapered shape and a forward tapered shape, and therefore the portions having a relatively low mechanical strength easily undergo bending deformation due to compression force. Accordingly, with the cover 200 of Embodiment 2, the possibility of buckling deformation during the application of compression force is reduced even further.

Embodiments 1 and 2 are merely examples. The present invention is not limited to Embodiments 1 and 2, and modifications can be made as appropriate.

In Embodiment 1, the compression units 110 and 120 include the first region that has a cylindrical shape and the second region that has a forward tapered shape, and in Embodiment 2, the compression units 110 and 120 include the first region that has a reverse tapered shape and the second region that has a forward tapered shape, but the configuration of the compression units is not limited to this. It is sufficient that a portion of a compression unit that has a relatively low mechanical strength undergoes bending deformation so as to become folded when subjected to compression force. Generally, if a compression unit has two or more regions whose outer faces or inner faces have different angles relative to the central axis 100a, this is advantageous in causing such bending deformation to occur. In Embodiments 1 and 2, the portions of the compression units that have a relatively low mechanical strength undergo bending deformation such that the outer face of the first region and the outer face of the second region come into contact, but they may undergo bending deformation such that the inner face of the first region and the inner face of the second region come into contact.

For example, a configuration is possible in which the first region has one of a forward tapered shape, a reverse tapered shape, and a cylindrical shape, and the second region has one of the two remaining shapes. Also, a configuration is possible in which both the first region and the second region have either a forward tapered shape or a reverse tapered shape, and the taper angle is different between the first region and the second region.

Also, the first region and/or the second region may have a shape other than a forward tapered shape, a reverse tapered shape, or a cylindrical shape. For example, a configuration is possible in which the inner faces of the first region and the second region are continuous cylindrical faces, the outer face of the first region is a reverse tapered face, and the outer face of the second region is a forward tapered face.

Furthermore, the compression units may be configured from three or more regions whose outer faces and/or inner faces have different shapes.

Instead of having a tapered shape or a cylindrical shape, the compression units may have a curved surface shape such that a cross-section including the central axis 100a of the compression unit is shaped as a "⊂", for example.

Although the outer circumferential wall 101 includes two compression units in Embodiments 1 and 2, the number of compression units configuring the outer circumferential wall 101 is not limited to two, and the number of compression units may be three or more. A higher number of compression units makes it easier to increase the amount of change in dimension of the cover during compression, and therefore this is advantageous in the case where the cover is attached to a long male member. Note that as the number of compression units increases, there is an increased possibility of the outer circumferential wall undergoing buckling deformation due to compression force. Accordingly, the number of compression units configuring the outer circumferential wall is preferably four or less, and more preferably two or three. If the number of compression units is three or more, thick portions and thin portions are formed such that portions having a large amount of change in dimension in the central axis 100a direction (portions having a relatively low mechanical strength) during compression and portions having a small amount of change in dimension in the central axis 100a direction (portions having a relatively high mechanical strength) during compression are formed so as to oppose each other in the up-down direction in mutually neighboring compression units.

There is no need for the diameters (sizes) of the plurality of compression units configuring the outer circumferential wall 101 to all be different. For example, the diameters of the plurality of compression units configuring the outer circumferential wall 101 may all be the same. Note that if the plurality of compression units having mutually different diameters are arranged in order of diameter magnitude in the central axis 100a direction, this is advantageous in that the amount of change in dimension during compression can be increased. If the plurality of compression units having different diameters are arranged such that the diameters of the compression units are higher the farther they are from the head portion 150 as in Embodiments 1 and 2, this is advantageous in that demolding is made easier in the case where the cover is formed using a mold, stability is improved in attachment of the cover using the base portion 180, and the size of the head portion 150 can be reduced.

Although both protruding portions (thick portions) and receding portions (thin portions) are formed in the compression units in Embodiments 1 and 2, either of them may be omitted. Even if either the protruding portions (thick portions) or the receding portions (thin portions) are omitted, the thickness of the compression units can be caused to periodically change in the circumferential direction, and the above-described effects of the present invention can be obtained. If both protruding portions (thick portions) and receding portions (thin portions) are formed, the protruding portions (thick portions) and the receding portions (thin portions) are arranged so as to alternate in the circumferential direction.

In contrast with Embodiments 1 and 2, the protruding portions (thick portions) may be formed on the inner faces of the compression units, and the receding portions (thin portions) may be formed on the outer faces of the compression units. Also, the protruding portions (thick portions) and the receding portions (thin portions) may be formed on the same faces (either the outer faces or the inner faces) of the compression units. Note that it is preferable that the protruding portions are formed on the outer faces of the compression units, and that the receding portions are formed on the inner faces of the compression units as in Embodiments 1 and 2 because this makes it possible to ensure a large space between the outer circumferential wall 101 and the male member. This is because the larger the space is between the outer circumferential wall 101 and the male member, the less likely it is for an impact to occur between the male member and the outer circumferential wall 101 that underwent deformation during compression, and therefore the amount of change in dimension of the cover overall can be increased.

A configuration is possible in which the protruding portions (thick portions) and the receding portions (thin portions) are formed on only a portion of the compression units in the central axis 100a direction. However, forming them over the full length of the compression units in the central axis 100a direction makes it possible to reduce deformation in a portion where deformation is not desired and to increase deformation in a portion where deformation is desired, and therefore this is advantageous in preventing buckling deformation of the outer circumferential wall 101 and increasing the amount of change in dimension during compression.

The number N of protruding portions (thick portions) and the number N of receding portions (thin portions) formed on the compression units does not need to be two as in Embodiments 1 and 2, and may be three or more. Note that as the number N increases, the amount of change in dimension of the cover during compression decreases. Accordingly, the number N is preferably four or less, and more preferably two or three.

In the case where N (N being a integer of two or more) protruding portions (thick portions) and/or receding portions (thin portions) are formed on each compression unit, the positions of the protruding portions (thick portions) and/or the receding portions (thin portions) are offset in the circumferential direction between two compression units that are neighboring in the central axis 100a direction. The offset amount between the protruding portions (thick portions) and/or between the receding portions (thin portions) between the two compression units that are neighboring in the central axis 100a direction is preferably 360/2N degrees with respect to the central axis 100a. Accordingly, portions having a large amount of change in dimension in the central axis 100a direction (portions having a relatively low mechanical strength) during compression and portions having a small amount of change in dimension in the central axis 100a direction (portions having a relatively high mechanical strength) during compression can be formed so as to oppose each other in the up-down direction between neighboring compression units.

Although the cross-sectional shape of the outer circumferential wall 101 along a plane perpendicular to the central axis 100a is a circle in Embodiments 1 and 2, the cross-sectional shape of the outer circumferential wall is not limited to this, and it may be a regular polygon such as a square or a regular hexagon, any polygon, a ellipse, or the like. Note that from the viewpoint of preventing buckling deformation of the outer circumferential wall, it is preferable that the cross-sectional shape of the outer circumferential wall is a circle.

The shape of the head portion 150 is not limited to the shape in Embodiments 1 and 2, and may be any shape. For example, it is possible to omit the mushroom-shaped apex portion 156 formed on the upper face 155 of the head portion 150. Note that the apex portion 156 has the following effects. As shown in FIGS. 9A and 9B, when the male luer 10 is inserted into the septum 951, the edge of the opening of the port cap 955 fits into the neck portion 158. Accordingly, as the male luer 10 is withdrawn from the needleless port 950 from the state shown in FIGS. 9A and 9B, the port cap 955 holds the head portion 150 so as to prevent the septum 951 and the apex portion 156 from separating. This is advantageous in causing the cover that underwent compression deformation to extend to its initial state. Also, since the septum 951 and the apex portion 156 separate after the male luer 10 has come out of the slit 153 in the head portion 150, less liquid remains on the surfaces of the septum 951 and the apex portion 156.

Figure 18:
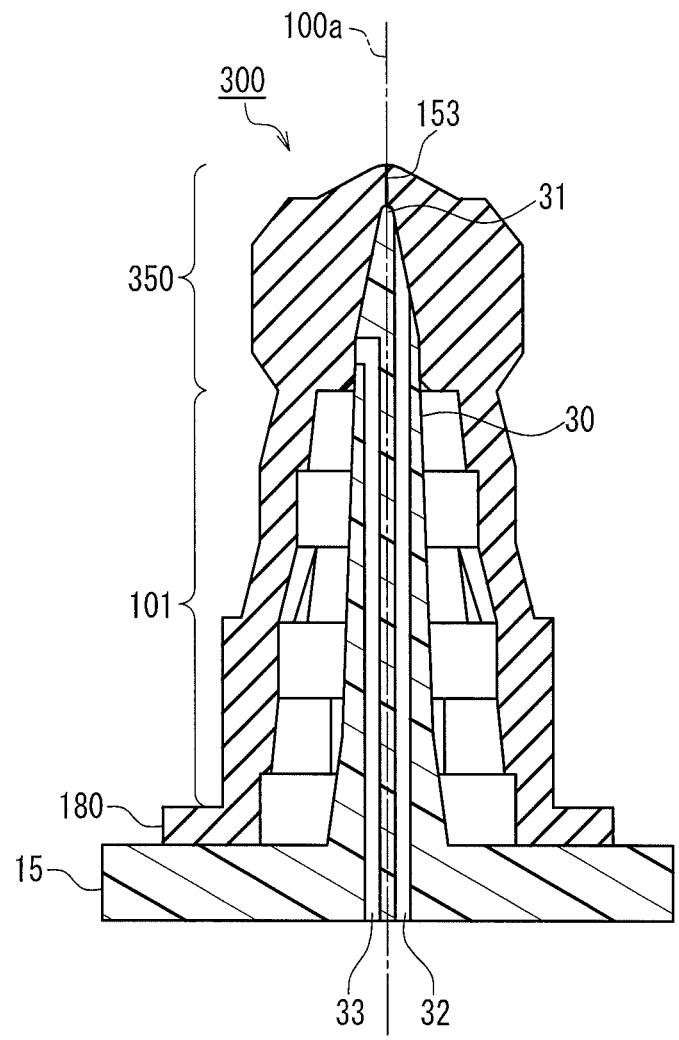
FIG. 18 is a cross-sectional view of a cover for a male member according to an embodiment of the present invention in a state of being attached to a bottle needle.

Although the male member is the male luer 10 that can be connected to a needleless port that includes a septum in Embodiments 1 and 2, the male member is not limited to this. For example, the male member may be a bottle needle that can puncture the rubber plug of a vial container. FIG. 18 is a cross-sectional view of a cover 300 according to an embodiment of the present invention in a state of being attached to a bottle needle 30. The bottle needle 30 generally includes a sharp tip 31 that can puncture a rubber plug, and is provided with two mutually independent flow channels 32 and 33 for air and for a liquid that extend in the lengthwise direction. The cover 300 is the same as the cover 100 of Embodiment 1 with the exception of the shape of a head portion 350. The tip 31 of the bottle needle 30 is inserted into the inner cavity of the head portion 350. The inner circumferential face of the inner cavity is in close contact with the tip 31 of the bottle needle 30 and the outer surface in the vicinity thereof, and blocks the openings of the flow channels 32 and 33. A slit 153 for passage of the bottle needle 30 is formed in the tip of the head portion 350. The various modifications described above can be applied to the cover 300.

INDUSTRIAL APPLICABILITY

Although there are no particular limitations on the field of application of the present invention, it can be used as a cover that is attached to a male member used in a transport line for giving an infusion or blood transfusion or performing extracorporeal blood circulation. The present invention also can be applied as a cover that is attached to the male member of various types of connectors used when preparing drug solutions or the like to be given to a patient. In particular, the present invention can be preferably used in fields that handle dangerous drugs (e.g., anticancer drugs), blood, and the like that need to be prevented from leaking or evaporating. Furthermore, the present invention can be used as a cover that is attached to a male member used in various types of fields that handle liquids for uses other than medical use, such as food substances.

DESCRIPTION OF REFERENCE NUMERALS

10 Male luer (male member)
30 Bottle needle (male member)
11, 32, 33 Male member flow channel
100, 200, 300 Cover for a male member
101 Outer circumferential wall
150, 350 Head portion
151 Inner cavity
110, 120 Compression unit
111a, 112a, 121a, 122a, 211a, 221a Outer face
111b, 112b, 121b, 122b, 211b, 221b Inner face
111, 121 Cylindrical shape
112, 122 Forward tapered shape
113, 123 Protruding portion (thick portion)
114, 124 Receding portion (thin portion)
211, 221 Reverse tapered shape

The invention claimed is:

1. A cover for a male member that is configured to cover at least a tip of a bar-shaped male member in which a flow channel for flow of a liquid is formed, the cover for a male member comprising:

an outer circumferential wall that has a substantially tubular shape and is capable of elastic compression deformation in a central axis direction of the cover, and a head portion that is provided at one end of the outer circumferential wall and is passed through by the tip of the male member when the outer circumferential wall undergoes compression deformation, wherein the outer circumferential wall comprises a plurality of compression units arranged along the central axis direction, the plurality of compression units each undergo deformation due to compression force in the central axis direction, letting N be an integer of 2 or more, the plurality of compression units each have N thick portions formed at equiangular intervals with respect to the central axis, or have N thin portions formed at equiangular intervals with respect to the central axis, or have both N thick portions and N thin portions formed at equiangular intervals with respect to the central axis, the thickness of each of the plurality of compression units periodically changes in a circumferential direction, and a phase with respect to the central axis of the periodic change in thickness is shifted between two compression units that are neighboring in the central axis direction.

2. The cover for a male member according to claim 1, wherein the N thick portions are each a rib-shaped protruding portion that extends in a direction parallel to the central axis direction.

3. The cover for a male member according to claim 1, wherein the N thin portions are each a groove-shaped receding portion that extends in a direction parallel to the central axis direction.

4. The cover for a male member according to claim 1, wherein at least one of the N thick portions and the N thin portions extend over the full length of the compression unit in the central axis direction on which they are formed.

5. The cover for a male member according to claim 1, wherein the N thick portions are formed on an outer face of the outer circumferential wall.

6. The cover for a male member according to claim 1, wherein the N thin portions are formed on an inner face of the outer circumferential wall.

7. The cover for a male member according to claim 1, wherein the plurality of compression units each comprise a forward tapered shape with an outer face and an inner face that are both forward tapered faces such that the diameters increase with increasing distance from the head portion.

8. The cover for a male member according to claim 7, wherein the plurality of compression units each comprise a cylindrical shape with an inner face and an outer face that are both cylindrical faces, on the head portion side relative to the forward tapered shape.

9. The cover for a male member according to claim 7, wherein the plurality of compression units each comprise a reverse tapered shape with an inner face and an outer face that are both reverse tapered faces such that the diameters decrease with increasing distance from the head portion, on the head portion side relative to the forward tapered shape.

10. The cover for a male member according to claim 1, wherein the plurality of compression units have substantially similar shapes, and a plurality of compression units having different diameters are arranged such that the diameters of the compression units are higher the farther the compression units are from the head portion.

11. The cover for a male member according to claim 1, wherein a cross-sectional shape of the outer circumferential wall along a plane perpendicular to the central axis at an arbitrary position on the central axis is substantially a circle.

12. The cover for a male member according to claim 1, wherein a phase of the periodic change in thickness is shifted by 360/2N degrees with respect to the central axis between two compression units that are neighboring in the central axis direction.

13. The cover for a male member according to claim 1,
wherein the head portion comprises an inner cavity that is configured to receive the tip of the male member, and when the tip of the male member is inserted into the inner cavity, the head portion blocks an opening of the flow channel formed in the male member.

14. The cover for a male member according to claim 1, wherein the male member is a male luer that comprises an outer circumferential face that is a cylindrical face or a tapered face.

15. The cover for a male member according to claim 1, wherein the male member is a bottle needle that comprises two mutually independent flow channels.

\* \* \* \* \*